United States Patent
Chen

(10) Patent No.: US 9,382,510 B2
(45) Date of Patent: Jul. 5, 2016

(54) METHODS AND DEVICES FOR ELECTROPORATION

(76) Inventor: Jian Chen, Blue Bell, PA (US)

(*) Notice: Subject to any disclaimer, the term of this patent is extended or adjusted under 35 U.S.C. 154(b) by 0 days.

(21) Appl. No.: 13/594,730

(22) Filed: Aug. 24, 2012

(65) Prior Publication Data

US 2013/0052711 A1 Feb. 28, 2013

Related U.S. Application Data

(60) Provisional application No. 61/527,357, filed on Aug. 25, 2011.

(51) Int. Cl.
*C12M 1/42* (2006.01)
*C12N 13/00* (2006.01)
*C12N 15/87* (2006.01)

(52) U.S. Cl.
CPC .............. *C12M 35/02* (2013.01); *C12N 13/00* (2013.01); *C12N 15/87* (2013.01)

(58) Field of Classification Search
CPC ........ C12M 35/02; C12N 13/00; C12N 15/87
USPC .......... 435/285.2, 283.1, 303.1, 305.1–305.4; 422/500, 503, 547, 551, 553
See application file for complete search history.

(56) References Cited

U.S. PATENT DOCUMENTS

| | | | |
|---|---|---|---|
| 5,232,856 A | 8/1993 | Firth | |
| 5,283,194 A | 2/1994 | Schmukler | |
| 5,422,272 A | 6/1995 | Papp | |
| 6,001,617 A * | 12/1999 | Raptis | 435/285.2 |
| 6,090,617 A | 7/2000 | Meserol | |
| 6,258,592 B1 | 7/2001 | Ragsdale | |
| 6,562,604 B2 | 5/2003 | Rubinsky | |
| 6,582,964 B1 * | 6/2003 | Samsoondar et al. | 436/67 |
| 6,617,154 B1 | 9/2003 | Meserol | |
| 6,705,463 B1 * | 3/2004 | Bucholtz et al. | 206/315.9 |
| 6,969,604 B1 | 11/2005 | Yakovenko | |
| D564,100 S | 3/2008 | O'Banion | |
| 7,358,077 B2 | 4/2008 | Zimmermann | |
| 7,678,564 B2 | 3/2010 | Muller-Hartmann | |
| 7,718,409 B2 | 5/2010 | Rubinsky | |
| 7,846,731 B2 | 12/2010 | Iwata | |

(Continued)

FOREIGN PATENT DOCUMENTS

WO  WO 2007/021994      2/2007
WO  WO 2008/051169 A1   5/2008

OTHER PUBLICATIONS

Johnson, Brent, Divine Spark, http://www.the-scientist.com/?articles.view/articleNo/19682/title/Divine-Spark/.*

(Continued)

*Primary Examiner* — Nathan Bowers
*Assistant Examiner* — Timothy Barlow
(74) *Attorney, Agent, or Firm* — Anova Law Group, PLLC

(57) ABSTRACT

An apparatus for electroporation of biological cells is provided. The apparatus includes a sample container having an insulator chamber for holding the cells. The sample container has a first electrode and a second electrode to provide electrical connection for electroporation. The insulator chamber is configured to contain at least one cell monolayer. The apparatus also includes a pulse generator that can generate a predetermined pulse for electroporation of the cells.

9 Claims, 16 Drawing Sheets

(56) References Cited

U.S. PATENT DOCUMENTS

| | | | |
|---|---|---|---|
| 8,222,014 B2 | 7/2012 | Firth | |
| 2004/0241783 A1* | 12/2004 | Papkovsky et al. | 435/288.4 |
| 2005/0170510 A1* | 8/2005 | Huang et al. | 435/459 |
| 2005/0282265 A1* | 12/2005 | Vozza-Brown et al. | 435/285.2 |
| 2007/0275454 A1 | 11/2007 | Chang | |
| 2009/0053813 A1* | 2/2009 | Evans | 435/285.2 |
| 2009/0209017 A1 | 8/2009 | Ragsdale | |
| 2009/0269851 A1 | 10/2009 | Ragsdale | |
| 2009/0305380 A1 | 12/2009 | Ragsdale | |
| 2010/0160850 A1 | 6/2010 | Ivorra | |
| 2011/0014701 A1* | 1/2011 | Ghosh | 435/374 |
| 2011/0118811 A1* | 5/2011 | VillemeJane et al. | 435/285.2 |
| 2011/0263005 A1 | 10/2011 | Chang | |

OTHER PUBLICATIONS http://www.sigmaaldrich.com/life-science/cell-culture/classical-media-salts/dmem.html (Feb. 2009).*

Kim et al., Electroporation of extraneous proteins into CHO cells: increased efficacy by utilizing centrifugal force and microsecond electrical pulses, Experimental Cell Research; 197(2):207-12; Dec. 1991.*

Canatella PJ, Karr JF, Petros JA, & Prausnitz MR, Quantitative study of electroporation-mediated molecular uptake and cell viability, 80 Biophysical J. 755 (2001).

Pavlin M, Pavselj N, & Miklavcic D, Dependence of induced transmembrane potential on cell density, arrangement, and cell position inside a cell system, 49 IEEE Transactions on Biomedical Eng'g. 605 (2002).

Neumann E, Schaefer-Ridder M, Wang Y, & Hofschneider PH, Gene transfer into mouse lyoma cells by electroporation in high electric fields, 1 EMBO J., 841 (1982).

Bockmann RA, De Groot BL, Kakorin S, Neumann E, & Grubmuller H, Kinetics, statistics, and energetics of lipid membrane electroporation studied by molecular dynamics simulations, 95 Biophysical J., 1837 (2008).

Sukhorukov VL, et al., Surviving high-intensity field pulses: strategies for improving robustness and performance of electrotransfection and electrofusion, 206 J. Membrane Biology, 187 (2005).

Golzio M, Teissie J, & Rols MP, Direct visualization at the single-cell level of electrically mediated gene delivery, 99 Proceedings of Nat'l Acad. of Scis. USA, 1292 (2002).

Zimmermann U, et al., Electromanipulation of Mammalian Cells: Fundamentals and Application, 28 IEEE Transactions on Plasma Science, 72 (2000).

Kim JA, et al. A novel electroporation method using a capillary and wire-type electrode, 23 Biosensors & Bioelectronics, 1353 (2008).

Kim JA, et al., A multi-channel electroporation microchip for gene transfection in mammalian cells. 22 Biosensors & Bioelectronics, 3273 (2007).

Shin YS, et al., Electrotransfection of mammalian cells using microchannel-type electroporation chip, 76 Analytical Chemistry, 7045 (2004).

Pucihar G, Kotnik T, Teissie J, & Miklavcic D, 36 Electropermeabilization of dense cell suspensions, European Biophysics J., 173 (2007).

Valic B, et al., Effect of electric field induced transmembrane potential on spheroidal cells: theory and experiment, 32 European Biophysics J., 519 (2003).

Egger M & Donath E, Electrorotation of dumb-bell shaped particles Theory and experiment, 26 Bioelectrochemistry and Bioenergetics, 383 (1991).

Abidor IG, Li LH, & Hui SW, Studies of cell pellets: I. Electrical properties and porosity, 67 Biophysical J., 418 (1994).

Abidor IG, Li LH, & Hui SW, Studies of cell pellets: II. Osmotic properties, electroporation, and related phenomena: membrane interactions, 67 Biophysical J., 427 (1994).

Gaynor PT & Bodger PS, Physical modelling of electroporation in close cell-to-cell proximity environments, 51 Physics in Medicine and Biology, 3175 (2006).

Pavlin M & Miklavcic D, Effective Conductivity of a Suspension of Permeabilized Cells: A Theoretical Analysis. Biophysical J., 719 (2003).

Susil R, Semrov D, & Miklavcic D., Electric field-induced transmembrane potential depends on cell density and organization, 17 Electro- and Magnetobiology, 391 (1998).

Gowrishankar TR, Stewart C, & Weaver JC., Electroporation of a multicellular system: asymptotic model analysis, Proceedings of the 26th Annual International Conference of the IEEE EMBS, 5444 (2004).

Gowrishankar TR & Weaver JC (2003) An approach to electrical modeling of single and multiple cells. Proc Natl Acad Sci U S A 100(6):3203-3208.

Tekle E, Astumian RD, & Chock PB., Electroporation by using bipolar oscillating electric field: an improved method for DNA transfection of NIH 3T3 cells, 88 Proceedings of Nat'l Acad. of Scis. USA, 4230 (1991).

Abidor IG, et al., Electrical properties of cell pellets and cell electrofusion in a centrifuge, 1152 Biochimica et Biophysica Acta, 207 (1993).

Li LH, et al., Electrofusion between heterogeneous-sized mammalian cells in a pellet: potential applications in drug delivery and hybridoma formation, 71 Biophysical J., 479 (1996).

* cited by examiner

METHODS AND DEVICES FOR ELECTROPORATION

CROSS-REFERENCES TO RELATED APPLICATIONS

This application claims priority of U.S. Provisional Patent Application No. 61/527,357, filed on Aug. 25, 2011, the entire contents of which are incorporated by reference herein.

FIELD OF INVENTION

This invention relates generally to methods and devices for electrical stimulation of cells and, more particularly, to methods and devices for electroporation of cells.

BACKGROUND

Electroporation is a widely-used method for permeabilization of cell membranes by temporary generation of membrane pores with electrical stimulation. The applications of electroporation include the delivery of DNA, RNA, siRNA, peptides, proteins, antibodies, drugs or other substances to a variety of cells such as mammalian cells, plant cells, yeasts, other eukaryotic cells, bacteria, other microorganisms, and cells from human patients. Electrical stimulation may also be used for cell fusion in the production of hybridomas or other fused cells. Electrical cell fusion may be regarded as a special form of electroporation.

During a typical electroporation, cells are suspended in a buffer or medium that is favorable for cell survival. For bacterial cells electroporation, low conductance medium, such as water, is often used to reduce the heat production by transient high current. The cell suspension is then placed in a rectangular cuvette embedded with two flat electrodes for an electrical discharge. For example, Bio-Rad (Hercules, Calif.) makes Gene Pulser line of products to electroporate cells in cuvettes. Traditionally, electroporation requires high field strength.

The electroporation process is usually toxic to the cells. First, when the electric field strength is too high, the cell membranes may be irreversibly damaged. Secondly, while electrically induced membrane pores allow a target substance to enter the cells, the pores may also allow outflow of cellular contents and inflow of other unintended substances which could negatively affect cell viability. Thirdly, the heat generated by the electric current may harm the cells. Lastly, electrochemically generated toxic agents such as free radicals, gas and metal ions near the electrodes are harmful to the cells.

Variation of cellular properties, i.e., heterogeneity of cells during electroporation remains the biggest hurdle for achieving high-efficiency electroporations with low cellular toxicities. One known factor contributing to the heterogeneity is cell size. Larger cells tend to be easier to be electroporated. For a mixture of cells with different sizes, when larger cells are efficiently electroporated under certain voltage, the voltage is often not sufficient to electroporate smaller cells efficiently. At a field strength that smaller cells are efficiently electroporated, larger cells are usually irreversibly damaged because the voltage is usually too high for the larger cells to survive. Other factors, such as different cell membrane composition or cell maturity, may also contribute to the heterogeneity of cells.

Despite of numerous attempts to improve the efficiency of cell electroporations, the critical problem of cell heterogeneity remains unsolved. The efficiency, cell survivability and cost effectiveness of electroporation methods can be further improved. The disclosed devices and methods are directed at solving one or more problems set forth above and other problems.

BRIEF SUMMARY OF THE DISCLOSURE

One aspect of the present disclosure provides an apparatus for electroporation of biological cells. The apparatus includes a sample container having an insulator chamber for holding the cells. The sample container has a first electrode and a second electrode to provide electrical connection for electroporation. The insulator chamber is configured to contain at least one cell monolayer. The apparatus also includes a pulse generator that can generate a predetermined pulse for electroporation of the cells.

Another aspect of the present disclosure provides an apparatus for electroporation of biological cells. The apparatus includes a sample container for holding a sample of biological cells for electroporation. The container includes an insulator chamber that forms the body of the container to hold the cells. The insulator chamber has a plurality of sides. The container also includes a first electrode and second electrode to receive an electrical pulse from an electrical pulse generator to electroporate the cells. The insulator chamber and the electrodes are able to seal the sample of biological cells within the sample container.

Another aspect of the present disclosure provides a process for electroporation of biological cells. The process includes the following steps. The cells are arranged to form at least one cell monolayer in an insulator chamber of a sample container. The sample container has a first electrode and a second electrode to provide electrical connection for electroporation. The cells in the cell monolayer are treated with a predetermined electrical pulse, which is generated by a pulse generator.

Other aspects of the present disclosure can be understood by those skilled in the art in light of the description, the claims, and the drawings of the present disclosure.

DETAILED DESCRIPTION

Reference will now be made in detail to exemplary embodiments of the invention, which are illustrated in the accompanying drawings. Wherever possible, the same reference numbers will be used throughout the drawings to refer to the same or like parts.

Figure 1A:
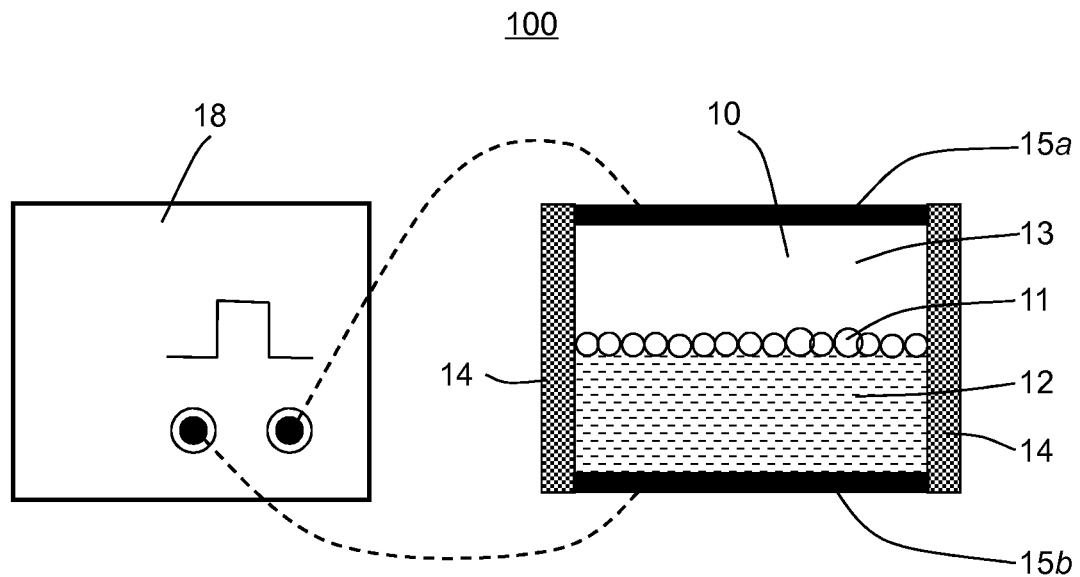
FIG. 1A illustrates an exemplary apparatus for electroporation of biological cells consistent with the disclosed embodiments.
Figure 1B:
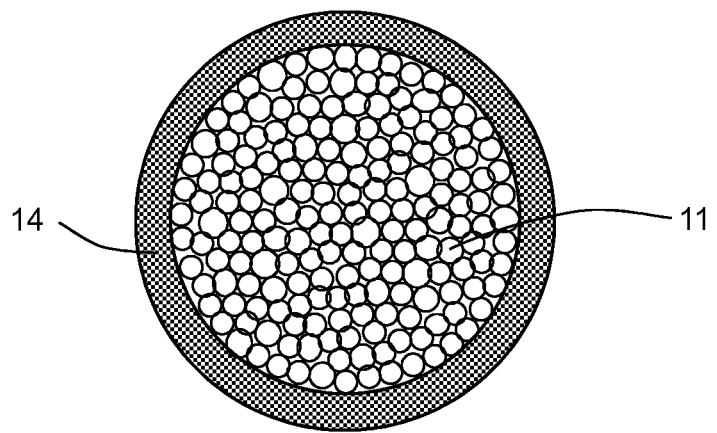
FIG. 1B illustrates an exemplary cell monolayer formed in an exemplary sample container consistent with the disclosed embodiments.

FIG. 1A illustrates an exemplary electroporation apparatus 100 consistent with the disclosed embodiments. The apparatus 100 includes a sample container 10. The sample container 10 includes an insulator chamber 14, a first electrode 15a, and a second electrode 15b. Within the sample container 10, an interface is formed on the surface of a lower medium layer 12 and below an upper medium layer 13. A cell monolayer 11 across the electric current field may be formed on the interface. A cell monolayer, as used in this disclosure, refers to a single, compactly packed layer of cells. A cell monolayer is therefore sometimes referred to as a compact cell monolayer, or a compact monolayer. The apparatus 100 also includes a pulse generator 18. The sample container 10 may be placed in the pulse generator 18, which delivers an electrical pulse through the first electrode 15a and the second electrode 15b. FIG. 1B provides a cross section view of the cell monolayer 11 within the insulator chamber 14. As shown in FIG. 1B, the monolayer 11 occupies the cross section area of the insulator chamber 14.

Figure 2A:
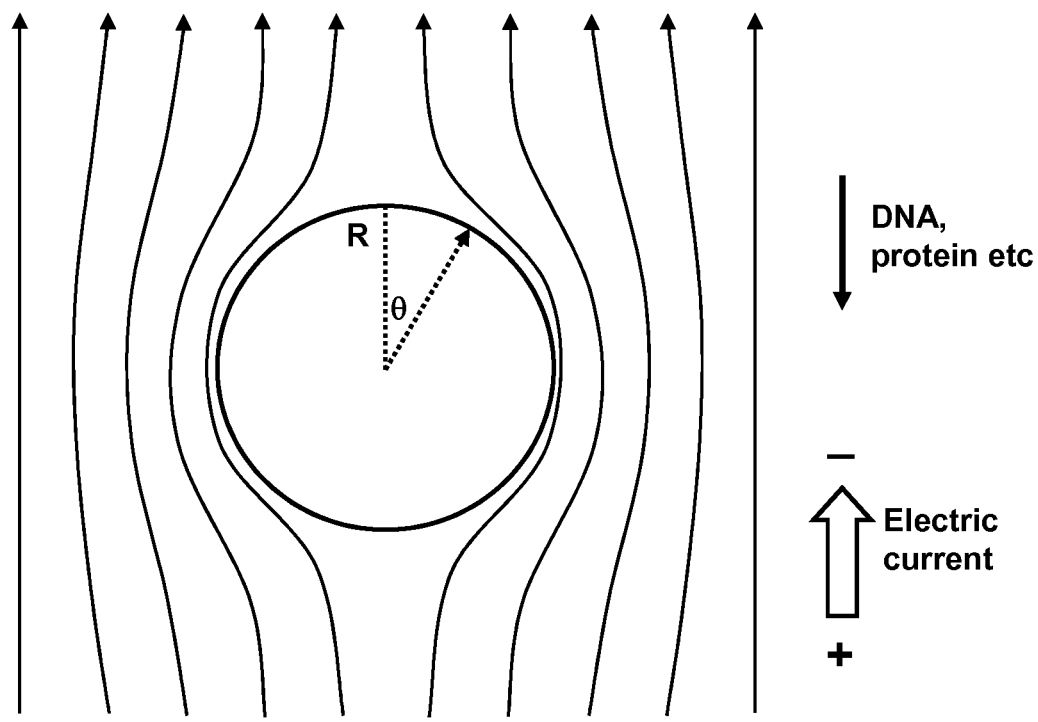
FIG. 2A illustrates the blocking and diverting effect on the electric current flow by a spherical insulator cell.

Apparatus 100 may be implemented using certain concepts for modeling cell electroporation. FIG. 2A illustrates the effect of a spherical cell with the radius R on the electric current flow or electric field that was originally uniform. For a typical electroporation such as delivery of DNA, RNA or proteins to cells, the electric shock takes place in a medium or other saline buffer solutions. Compared to extracellular solution and intracellular cell plasma, the lipid-bilayer based cell membrane has much lower electric conductance and most of the electric current bypasses the interior of the cells. A cell is thus similar to an insulator object.

The insulator effect of the cell membrane protects the cell interior from a short-time exposure of strong electric field during electroporation. As shown in FIG. 2A, the blockade and diversion of the electric current by an insulator-like spherical cell changes a uniform electric field to one that is bulged around the cell.

A local point on the cell membrane can be designated by its radius angle θ from the direction of general electric current. The negatively charged molecules such as DNA, RNA and proteins in a conductive medium move in the opposite direction to that of the electric current.

For a single cell with a radius of R placed in an originally uniform electric-current field, the transmembrane potential at a given point on the membrane with a radius angle θ can be roughly modeled by the equation $$V_\theta = 1.5 \cdot E_0 \cdot R \cdot \cos \theta \quad (I),$$

where $E_0$ is the field strength of the original uniform electric field. When θ equals to 0° or 180° at the two topical points relative to the direction of the overall electric field, cos θ equals to 1 or −1 and the transmembrane potential value is the highest. At the topical point downstream of electric current (θ=0°) but not upstream of electric current (θ=180°), negatively charged molecules such as DNA, RNA and proteins pass through the membrane under the greatest electrical potential. On the contrary, the transmembrane potential is zero at the points on the cell membrane where θ equals 90°, although the electric current is strongest just outside these membrane points.

The transmembrane potential is largest when θ is 0° and decreases to zero potential when θ is 90°. A larger transmembrane potential at a local membrane point can produce a larger force to transport molecules. To deliver a substance, a minimal transmembrane potential $V_{min}$ would be required. A maximal value of θ, or $\theta_{max}$ could be reached between 0° and 90° where the transmembrane potential becomes $V_{min}$. Meanwhile, the transmembrane potential on cell points with smaller θ cannot be higher than the potential that could irreversibly damage the cell. The $\theta_{max}$ defines the largest effective electroporation surface.

Figure 2B:
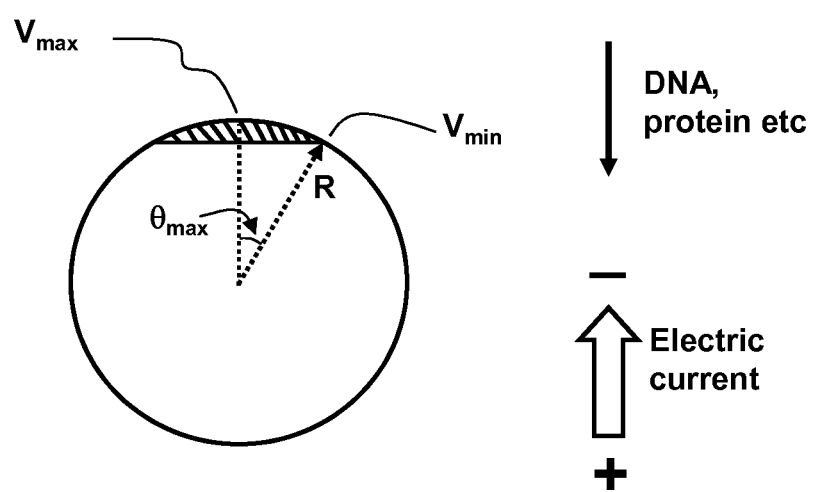
FIG. 2B illustrates the effective surface for electroporation on a cell.

FIG. 2B illustrates the effective electroporation surface (represented by the shaded area) on a spherical cell. The effective electroporation surface, or the effective surface for electroporation, as used in this disclosure, refers to the portion of cell surface that has sufficient transmembrane potential to allow exogenous substances, such as DNA, RNA, or proteins, to enter the cells. In an electroporation to introduce large molecules such as DNA, RNA or proteins to the cells, the cells can survive only under certain transmembrane potential. In FIG. 2B, $V_{max}$ represents the maximally tolerable reversible transmembrane potential, above which a cell would be irreversibly damaged. $V_{min}$ represents the minimally permeable transmembrane potential that allows effective electroporation, below which the exogenous substance cannot enter the cell. Both $V_{max}$ and $V_{min}$ are determined by the membrane characteristics. $V_{max}$ would be the same regardless of the kind of target substance to be delivered, whereas $V_{min}$ is related to the target molecular properties such as size and electric charge. Larger molecules would probably have larger $V_{min}$ for delivery. The window between $V_{max}$ and $V_{min}$, which is the effective range of the transmembrane potential to electroporate the cell, may be small especially for delivering larger molecules.

As shown in FIG. 2B, only the topical point of the cell can reach $V_{max}$, the highest transmemberane potential. The outer boundary of the shaded effective electroporation surface has the transmembrane potential of $V_{min}$ and the radius angle of $\theta_{max}$. For negatively charged molecules such as DNA, RNA and proteins, the effective electroporation surface is located downstream of the electric current.

At the topical point, $$\theta = 0° \text{ and } \cos \theta = 1,$$

giving $$V_{max} = 1.5 \cdot E_0 \cdot R.$$

At $\theta_{max}$ where transmembrane potential decreases to $V_{min}$, $$V_{min} = 1.5 \cdot E_0 \cdot R \cdot \cos \theta_{max} = V_{max} \cdot \cos \theta_{max}.$$

Therefore $\theta_{max}$ is determined by satisfying $$\cos\theta_{max} = V_{min}/V_{max}.$$

According to this modeling, the topical point has the highest rate of effective molecular transport. The local transportation rate decreases with the increase of $\theta$ until it becomes zero at $\theta_{max}$.

When individual cells of different radius are placed in a uniform electric field, each cell has a different transmembrane potential profile. The absolute values of $V_{min}$ and $V_{max}$ are subject to certain variations according to circumstances. For example, when different electrical pulse shapes such as exponential decay wave or square wave are used, $V_{min}$ and $V_{max}$ values might be different. However, the ratio of $V_{min}/V_{max}$ is probably not as sensitive to these types of alterations.

Figure 3:
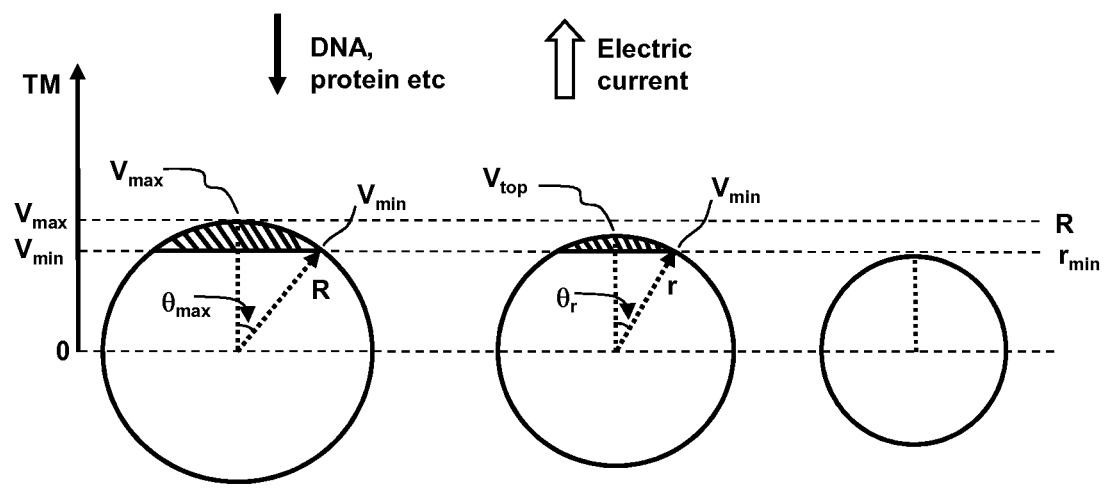
FIG. 3 illustrates the effect of cell size on the effective electroporation surface.

FIG. 3 illustrates how cell size affects the effective electroporation surface. The cell membrane is essentially a lipid bilayer dotted with membrane proteins including some channels. Cells of the same type have similar membrane compositions although the cell size varies to some extent. Therefore, electrical properties of the membrane such as $V_{max}$ and $V_{min}$ may be considered identical on different local point of a cell and for the cells of the same type but of different size. Even for different cell types, many mammalian cells probably share similar membrane electric properties including $V_{max}$ and $V_{min}$ since the membranes are essentially a lipid bilayer similarly dotted with different proteins.

As shown in FIG. 3, three individual free cells, a large one on the left with the radius "R", an intermediate one in the middle with the radius "r" and a small one on the right are analyzed. The three cell centers are aligned so that the circles can represent either the physical cells or transmembrane potential profiles. The electric field strength is set for the large cell to reach $V_{max}$ at the topical point, and the effective electroporation surface is shaded between the topical point with $V_{max}$ and the outer boundary with $V_{min}$. When the large cell obtains optimal electroporation, $$V_{max} = 1.5 \cdot E_0 \cdot R$$

giving $$E_0 = V_{max}/(1.5 \cdot R).$$

The intermediate cell (radius $r<R$) would have a lower transmembrane potential and at the topical point. The transmembrane potential $V_{top}$ at the topical point is given as $$V_{top} = 1.5 \cdot E_0 \cdot r = V_{max} \cdot r/R.$$

The effective surface for the intermediate cell with transmembrane potential larger than $V_{min}$ is defined by the outbound angle $\theta_r$ satisfying $$V_{min} = 1.5 \cdot E_0 \cdot r \cdot \cos\theta_r = V_{top} \cdot \cos\theta_r = (V_{max} \cdot r/R) \cdot \cos\theta_r,$$

giving $$\cos\theta_r = (V_{min}/V_{max}) \cdot (R/r).$$

The effective electroporation surface on the intermediate cell is smaller than that of the large cell and it is shaded between the topical point with $V_{top}$ and the outer boundary with $V_{min}$. When $r/R = V_{min}/V_{max}$, $\cos\theta_r$ becomes 1 and the effective surface diminishes to zero. Therefore the minimum radius of cell to obtain effective electroporation is $$r_{min} = (V_{min}/V_{max}) \cdot R.$$

The small cell shown on the right with a radius less than $r_{min}$ would not have any point reaching $V_{min}$ and there is no effective electroporation surface.

Therefore, cell size is an important factor in electroporation. Larger cells not only have higher transmembrane potential at the topical point but also larger effective surface. When a higher electric current field is applied so that the transmembrane potential of a smaller cell can reach $V_{max}$, a larger cell may not be able to survive. The difference in cell size is unavoidable and accounts for some heterogeneity of cellular properties in electroporation. For example, if 95% of a cell population has a radius variation of about 20% with normal (Gaussian) distribution, and $V_{min}/V_{max}$ (i.e., $r_{min}/R$) is about 90%, only the cells within a range of a radius variation of about 10% may be effectively electroporated. Based on Gaussian distribution, the highest theoretical electroporation efficiency is about 67.3% when the midsized cells are electroporated. For larger molecules, $V_{min}/V_{max}$ (i.e., $r_{min}/R$) is about 95%, the highest theoretical electroporation efficiency becomes about 37.6%.

The cell size problem also extends to different cell types. Since many types of mammalian cells would have similar $V_{min}$ and $V_{max}$, cell types of smaller sizes require much higher electric current field strength to reach $V_{min}$ and often the toxicities related to high electric current such as heat, free radicals, gas and metal ions may irreversibly damage the cells before they are effectively electroporated. Cell size cannot be easily changed, so an electroporation method that accommodates the variability in cell size is desirable but not currently available.

The above analysis of the transmembrane potential of individual ideal cells lays down the foundation for understanding cell electroporation. In an electroporation, it is often desirable to use a large number of cells in the order of $10^6$ to $10^7$. The cells are also crowded in a small volume mainly for two reasons: i) to achieve a high concentration of a target substance to be delivered, ii) a smaller sample volume requires less energy and therefore the pulse generator is easier to manufacture.

In a typical electroporation with 10 million cells suspended in 0.2 ml medium, each cell occupies an average medium space of 20,000 cubic microns ($\mu m^3$). Each cell occupies a space equivalent to a cube with the side length of about 27 $\mu m$, not much larger than the diameter of typical mammalian cells. Therefore in a typical electroporation, the average distance between cells is comparable to the cell diameter of most mammalian cells, i.e., cells may be very close to each other.

The Equation (I) is valid only when a single free cell is placed in a uniform electric field. The Equation (I) can be roughly applied when a small number of cells are placed in a uniform electric field with the distance between them far exceeding the cell diameter. In an electroporation when cells are crowded, the electric field surrounding each cell is shaped by this cell itself and other cells in its proximity. While the inherent membrane properties $V_{min}$ and $V_{max}$ are still the same, the Equation (I) can no longer be applied to calculate the transmembrane potential at a given point. As a result, the profile of the electric field becomes very complicated and unpredictable. The random positioning of cells constitutes yet another layer of heterogeneity in electroporation efficiency of cells even if the cells are perfectly equal in size.

Thus, an analysis of the complex electric field is presented in order to better understand the electric field and to facilitate the design of improved methods of electroporation and electrical cell fusion.

Figure 4:
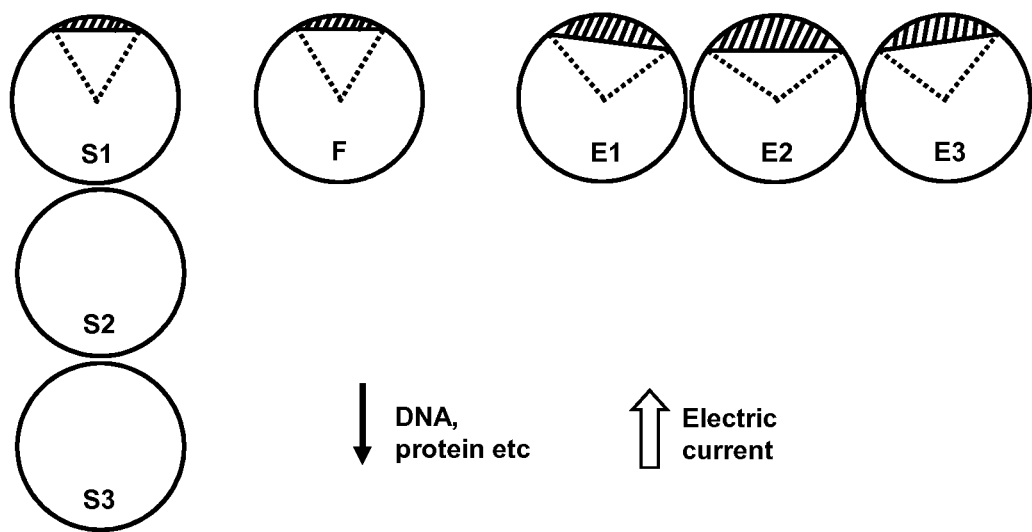
FIG. 4 illustrates three representative neighboring cell positions with the indicated direction of the electric current.

FIG. 4 illustrates three types of representative cell positioning with cells of an equal size. The first type is a free cell (F) not affected by neighboring cells. The second and third types represent two special ways of positioning neighboring cells. In the first special positioning, two or more cells closely line up in a longitudinal fashion along the direction of general electric current flow. This positioning is represented by cells S1, S2 and S3. In the second special positioning, cells are closely arranged laterally on a cross-sectional plane that is substantially perpendicular to the direction of general electric current flow. This positioning is represented by cells E1, E2 and E3. While it is more complex to derive the exact equations of the transmembrane potentials on these cells, a qualitative analysis can be done in a relevant and sufficient manner for developing improved methods of electroporation.

As shown in FIG. 4, S1, S2 and S3 are closely lined up and they do not block and divert the flow of electric current significantly more than the free cell F. Therefore, only S1 and S3 have a similar transmembrane potential profile on the topical surface to that of the cell F. Moreover, only the topical surface of the S1 cell downstream of the electric current (the shaded area in FIG. 4) would be effective for electroporation of negatively charged molecules. The S3 cell can be like the S1 cell for electroporation of negatively charged molecules if the direction of electric current is reversed. S2 cell would have lower transmembrane potential because of the shielding effect from S1 and S3 cells. The effect of a leading cell shielding the following cells from obtaining electroporation is defined as the longitudinal shielding effect. The longitudinal shielding effect becomes less prominent as the distance between cells increases or when the lineup deviates from the strict longitudinal orientation. The longitudinal lineup thus introduces a level of undesirable heterogeneity in electroporation by decreasing the efficiency of electroporation for many shielded cells.

On the contrary, the cells E1, E2 and E3 collectively exert a much bigger effect in blocking and restricting the flow of electric current. As a result, E1, E2 and E3 would have higher transmembrane potentials than that of the cell F just as if they formed an extra-large individual cell. The laterally arranged cells would no longer follow the transmembrane potential Equation (I). Because there is less overall electric current near the plane of cells, the transmembrane potential would decrease from the topical point more gradually than that of a free individual cell. In a qualitative description, each of the E1, E2 and E3 cells would have a larger effective electroporation surface than an F cell for an enhanced effect of electroporation between the points of $V_{max}$ and $V_{min}$, although the shape of the effective surface may become somewhat irregular.

While a three-dimensional contour map would describe the actual effective electroporation surface on E1, E2 and E3 more precisely, a two-dimensional shading as used in FIG. 4 suffices to roughly illustrate the increased effective surface area. The effect of laterally arranged cells enhancing each other's electroporation accessibility is defined as the lateral enhancing effect. The lateral enhancing effect becomes less prominent as the distance between cells increases or when the cells deviate from the cross-sectional planar positioning. Overall, these cells can be rated for electroporation accessibility at the indicated electric current direction as follows:

E2,E1,E3>S1,F>S2,S3

In a typical electroporation carried out in cell suspensions, the complex cell-to-cell electrical interactions can be characterized in three main categories: longitudinal shielding, lateral enhancing and hybrid interaction of longitudinal shielding and lateral enhancing. The hybrid interactions are between neighboring cells in a position that is neither predominantly longitudinal nor predominantly lateral and these interactions have less shielding or enhancing effect. The qualitative analysis revealed that longitudinal shielding is usually undesirable for achieving a high efficiency in electroporation. The effect of longitudinal shielding in a cell suspension is hard to avoid. Alternating the direction of electric current may present both topical surface of a longitudinal lined up cells for increased efficiency of electroporation. The lateral enhancing effect is beneficial for electroporation and especially helpful for difficult cell types of small sizes that require a destructively high electric field strength to reach $V_{min}$.

Based on these understandings, it becomes desirable to eliminate or diminish the undesirable longitudinal shielding effect and maximize the effect of lateral enhancing during electroporations.

Returning to FIG. 1A, when cells reside in the compact monolayer 11 across the electric current field, the longitudinal shielding effect is geometrically eliminated and the lateral enhancing effect is increased between cells.

As shown in FIG. 1A, the insulator chamber 14, the first electrode 15a, and the second electrode 15b seal the upper medium layer 13 and the lower medium layer 12 within the sample container 10 so that the sample would not leak. The container 10 may be in different shapes. For example, the container 10 may be cylindrical or non-cylindrical.

The insulator chamber 14 used in the sample container 10 may be made of nonconductive materials such as plastics, rubber, polystyrene, polypropylene, polyethylene, polycarbonate, polymethylmethacrylate, polyimide, polydimethylsiloxane, cyclic olefin copolymer, thermoplastic polyester elastomer, glass, quartz and silicon. The insulator chamber 14 may be made of one or more types of materials so that it can be strong and fit tightly with the electrodes.

The first electrode 15a and the second electrode 15b may be made of conductive materials such as aluminum, iron, steel, nickel, titanium, zinc, copper, tin, silver, graphite and alloys. They can also be made of gilded metals, surface-modified metals or nonconductive materials such as rubber or plastics coated or intermixed with conductive materials. The first electrode 15a and the second electrodes 15b may be made transparent for microscopic observation of cells using materials such as indium-tin oxide, aluminum-doped zinc oxide and antimony-doped tin oxide.

The electrode 15a may be an upper electrode, and the electrode 15b may be a lower electrode. The distance between the two electrodes 15a and 15b is preferred to be larger than 1 mm for easy handling of the liquid, and less than 50 mm to avoid consuming too much target substance to be delivered. In one embodiment, a distance between the two electrodes 15a and 1b is ranged from 1 mm to 30 mm for easy handling and conservation of reagents. The shape and dimension of the electrode plates 15a and 15b may be determined according to those of the container 10. Since the electric power used in the monolayer method is very low as discussed in the paragraphs [0071] to [0075] and little amount of metal ions is released, it is usually not necessary to use precious metals such as gold or platinum to make the electrodes 15a and 15b. However, precious and inert metals such as gold and platinum may be used to make the electrodes 15a and 15b when cost is not a concern or when the containers need to be reusable.

The pulse generator 18 generates an electrical pulse for electroporation of the biological cells. The generator 18 may generate one or several different pulse forms such as, exponential decay wave, square wave or rectangular wave, high-frequency waves, and a combination of multiple wave forms. The pulse forms for electroporation may be predetermined based on cell type, the type of the container, and/or other data. The pulse generator 18 may thus be programmed to deliver the predetermined pulse form for the electroporation. In this disclosure, a pulse, or a pulse form, may refer to a single pulse or a combinatorial pulse composed of multiple pulses or pulse forms.

The compact cell monolayer 11 can be formed on the surface of an electrode or anywhere between the two electrodes. To form a cell monolayer 11 that is not directly on an electrode, an interface can be made between the two conductive medium layers 12 and 13 for cells to stay on. A cell suspension containing an appropriate number of cells is placed on the surface of the lower medium layer 12. The cell suspension may be formed by suspending the cells in a medium or buffer used to form the upper medium layer 13 or other appropriate medium or buffer. The cells may settle to the interface between the lower medium layer 12 and the upper medium layer 13 by natural gravity or an artificial centrifuge force. The pulse generator 18 delivers a certain form of electrical pulse to the cell monolayer through the first electrode 15a and the second electrode 15b and the pulsing takes place after the cell monolayer is formed.

A stable interface needs to be maintained between the upper medium layer 13 and the lower medium layer 12 during electroporation. The upper medium or buffer layer 13 usually comes from the medium or buffer used to create the cell suspension or any other appropriate medium or buffer. The medium or buffer used in the upper medium layer 13 may be any suitable medium or buffer, such as MEM, DMEM, IMDM, RPMI, Hanks', PBS and Ringer's solution. The lower medium or buffer layer 12 may be a solution with a higher density such as solutions containing sugars, glycerol, polyethylene glycol (PEG) and ficoll. The medium or buffer used in the lower medium layer 12 may be any suitable medium or buffer, such as MEM, DMEM, IMDM, RPMI, Hanks', PBS and Ringer's solution, which may or may not be the same to the medium or buffer used in the upper medium layer 13. The lower medium layer 12 may also be formed from a semi-solid gel such as agar or agarose based gel, silicone gel, polyacrylamide gel, collagen or gelatin gel, matrigel, hyaluronic acid gel, alginate gel, polyethylene glycol gel, methyl cellulose or other modified cellulose based gel, acrylates gel, polyglycols gel and propylene glycol gel.

Furthermore, the lower medium layer 12 may be formed from a porous solid matrix doused with a medium or buffer. The solid matrix is porous and preferably hydrophilic so that conductivity of the lower medium layer 12 is maintained. The solid matrix may be made of materials such as silicone, resins, glass fibers, polymethacrylates, silicates, modified cellulose, polyvinyls, polylysine, polyacrylic acid, polyethylene glycol, polyacrylamides and co-polymers. Certain materials that form the lower medium layer 12 may falls between the physical states of liquid and semi-solid, or semi-solid and solid, or liquid and solid. Such physical state of the lower medium layer 12 would not affect electroporation as long as a stable interface may be formed and maintained between the upper medium layer 13 and the lower medium 12. The target molecules to be delivered may be in the upper medium layer 13, or the lower medium 12, or both.

The lower medium layer 12 that is semi-solid or solid may be pre-formed in the sample container 10. For example, an agarose gel in suitable medium, such as RPMI medium, may form the lower medium layer 12 and may be precast in the sample container 10.

Usually, two medium layers, an upper medium layer 13 and a lower medium layer 12 would be sufficient to form the cell monolayer 11 for electroporation. However, in certain embodiments, more than two conductive medium layers may be used as long as there is at least one medium interface for cells to stay on. Sample containers of different cross section area may be made to form interfaces with different sizes to accommodate different number of cells.

Figure 1C:
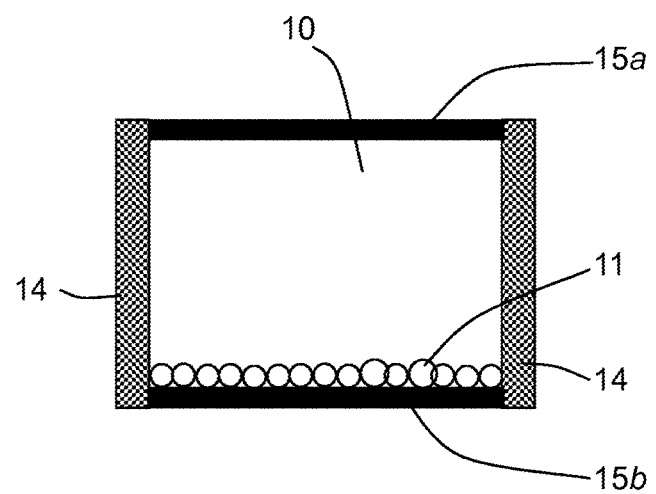
FIG. 1C illustrates an exemplary cell monolayer formed in an exemplary sample container consistent with the disclosed embodiments.

FIG. 1C illustrates an exemplary sample container consistent with the disclosed embodiments. As shown in FIG. 1C, the cell monolayer 11 is formed directly on the electrode 15b. To form the monolayer 11, a cell suspension with an appropriate number of cells in an appropriate medium or buffer is loaded in the sample container. The cells settle to the electrode 15b to form the monolayer 11 either under natural gravity or by centrifugation. This is suitable when the electric field strength required is low and/or the cells may tolerate the toxicities.

For electroporation of most eukaryotic cells, the medium or buffer that forms the two medium layers 12 and 13 usually contains salts to maintain a proper osmotic pressure. The salts in the medium or buffer also render the medium layers 12 and 13 conductive. For electroporation of very small prokaryotic cells such as bacteria, sometimes water is used as a low conductance medium to allow a very high electric field strength. In that case, the charged molecules to be delivered still render water based medium more conductive than the lipid based cell membranes and the medium may still be roughly considered as conductive especially compared to cell membranes.

The number of cells to be used to form the monolayer 11 is determined by the area of the surface where the monolayer 11 is located and the area occupied by an average sized cell. The cell concentration to be used may be empirically determined by observation of the monolayer 11 under microscope in another transparent container with a known area, by electrical resistance measurement or by testing of electroporation efficiencies with different cell numbers. Many mammalian cells may need a density of 0.2-2 million cells per square centimeter for a compact monolayer. The properties of different cells such as average area of occupancy and preferred electric field strength can be stored in a database for easy reference. Sample containers of different interface area can be made to accommodate different cell numbers.

Two or more monolayers of cells may stack up compactly on the medium interface and the resulted cell pellet can still be electroporated. In this situation, the electroporation may become more heterogeneous with increased variation of molecular transport among cells with the exception of a cell double layer. In a cell double-monolayer, the two monolayers of cells can still have quite homogeneous electroporation when an alternating current pulsing scheme is used. A pellet, as used in this disclosure, refers to a group of cells that form more than a single, compactly packed layer. The cells in a pellet may or may not form discernible layers.

Multiple monolayers of cells, also referred to as a cell pellet, can be conveniently used in applications that require a very high cell number and that the variation of molecular transport among cells is not a major concern. The multiple-monolayer method of electroporation can be considered as a special form or an extension of the monolayer electroporation method. Compared to traditional electroporation with a cell suspension, the multiple-monolayer method of electroporation is still advantageous in efficiency, cell survivability and cost effectiveness. The methods and devices described for a cell monolayer are all applicable to cells in multiple layers or in a pellet.

Figure 5:
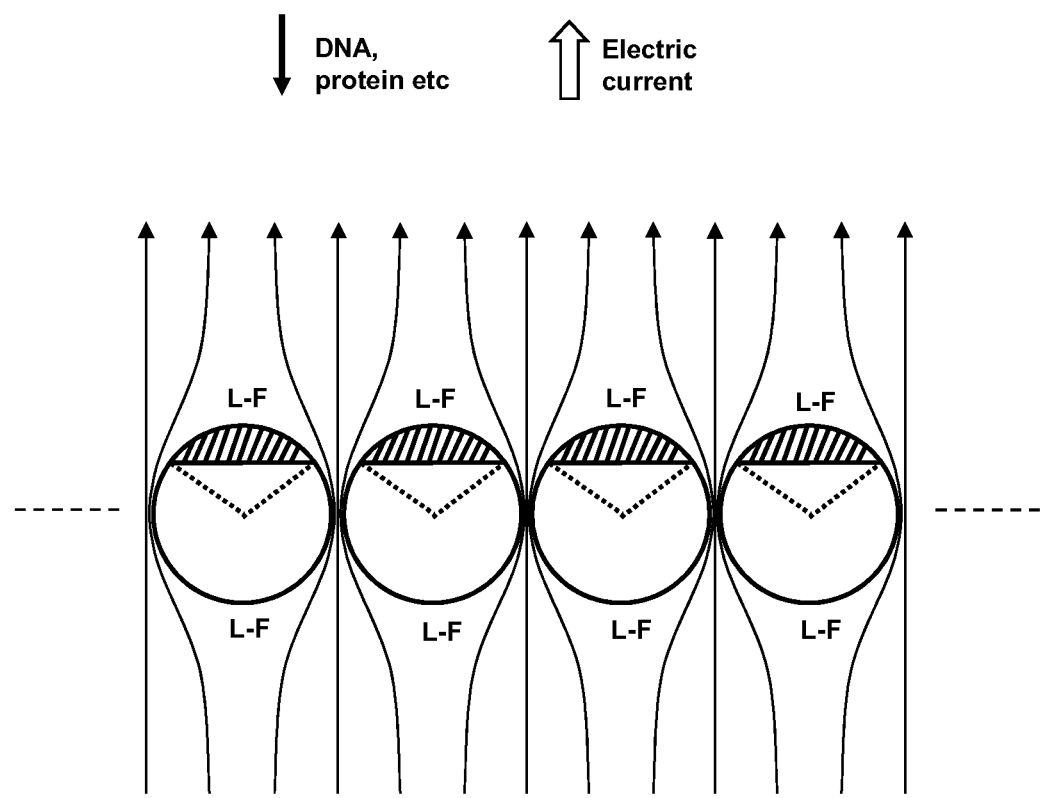
FIG. 5 illustrates the distribution of the electric current that flows through a cell monolayer.

The monolayer electroporation method substantially decreases the necessary overall electric field strength. FIG. 5 illustrates the distribution of the electric current that flows through the cell monolayer 11. In FIG. 5, the three-dimensional distribution of the electric current around a cell monolayer is illustrated by a simplified two-dimensional representation.

Because cells are similar to insulators, most of the electric current that goes through the compact cell monolayer 11 would go through the crevices between the cells. Only the electric current field strength within the crevices between the cells would be similar to what is needed for a traditional electroporation in a suspension. In other locations, the electric current is spread to a very low level.

Just outside the monolayer 11, the electric current density or the electric field strength is dispersed to a very low level, thus creating an enlarged region of low electric field (L-F) near the topical surfaces of the cells. Within the L-F regions, there is very little electric potential change regardless of the variation in cell sizes and crevice sizes, as long as the monolayer is compact and the crevices are relatively small. The shaded areas represent effective electroporation surfaces for negatively charged molecules at the given direction of electric current.

This is beneficial for cell survival since the space of the crevices are small and the effect of small regions of stronger current would quickly dissipate. A crevice between cells may have an irregular shape, therefore the width or the area of a crevice would not be uniform. The crevice width can be roughly defined as the average width of a electric current path below the effective electroporation surfaces.

For example, when the cells in the monolayer 11 occupy 80% of the space and leave about 20% the total crevice space between cells, the total electric current would be about 20% of what is required to generate a similar transmembrane potential for a suspension of these cells in the same container. The overall increase of electric resistance would be small, as the resistance of the monolayer 11 is about 5 cells' depth of medium (reciprocal of 20% is 5) and this is small compared to the usual distance between electrodes. This translates into about 20% of the voltage and only about 4% of the required power (20%×20%) for traditional electroporation in the same container. If the space between cells is 10% of the total space, the voltage required would be about 10% and the power required would be about 1%, and so on.

As used in this disclosure, the term "compact" refers to the extent that the cells occupy the monolayer area. The term "compactness," refers to the percentage of the cell monolayer area that is occupied by the cells. A reasonable minimal working compactness for the monolayer 11 would be around 50% to take advantage of the lateral enhancing effect. As the layer compactness increases, the lateral enhancing effect becomes more significant and beneficial. Complete compactness is reached when no more cells can fit into the monolayer at a given gravity or centrifugal force. At complete compactness, the total space between cells would be small but not totally eliminated. When cells are compactly arranged, they may not appear circular or spherical because of their plasticity. Slightly going over a complete compactness in the monolayer would cause a small decrease in efficiency, as a small portion of cells would lie on top of each other and introduce some undesirable longitudinal shielding effect.

Compared to free individual cells in a suspension, every cell in the compact monolayer 11 would have a larger effective surface. Within the effective surface, the transmembrane potential does not drop from the topical point as steeply as free individual cells. In traditional electroporation in a suspension, cells have heterogeneity in both transmembrane potential and effective delivery surface area. However, cells of variable size would have similar transmembrane potential in a compact monolayer. This is because overall current on both sides of the monolayer are small and therefore the potential is substantially equal just outside of the monolayer. A smaller cell in the monolayer 11 would have only smaller effective delivery surface, but almost equal transmembrane potential compared to larger cells.

With the monolayer method, the amount of target molecules delivered to each cell would be much less variable. For example, a 10% cell diameter difference may cause a difference greater than an order of 10 in substance delivery in traditional electroporation. By contrast, the variation in substance delivery may be about 10% in compact monolayer electroporation. Because of the more leveled electric potential profile on the topical surfaces, the working voltage range (percentage wise) is increased compared to a similar pulsing scheme in traditional methods.

Because low electric power is used in monolayer electroporation, many of the cell toxicities related to electric current and electrodes would be reduced. Directly arranging the compact monolayer 11 on the electrode 15b is relatively simple and it might be suitable for cells that require very small electric field strength in a certain buffer or for cells that can tolerate the toxicities. Using an interface between the conductive medium layers 12 and 13 may be advantageous, because physically keeping the cells away from the electrodes 15a and 15b is a very effective way of avoiding electrochemical toxicities to the cells. A conductive medium or buffer conducts electricity by solute ions and it is distinct from an electrode that typically conducts electricity by free electrons.

Also because the lower electric power is used in monolayer electroporation, it becomes easier to manufacture the pulse generator 18 for monolayer based electroporation method compared to making pulse generators for traditional electroporation methods. When the output power is lower, it is easier to generate different pulse forms. One type of common pulse form is the exponential decay wave, typically made by discharging a loaded capacitor to a sample. The exponential decay wave can be made less steep by linking an inductor to the sample so that the initial peak current can be attenuated. Another type of common pulse form is square wave or rectangular wave. Other waveforms such as high-frequency waves can also be easily generated when desired. A single waveform or multiple waveforms in a sequence can be applied to a sample.

When multiple waveforms in a specified sequence are used, they can be in the same direction (direct current) or different directions (alternating current). Using alternating current can be beneficial in that two topical surfaces of a cell instead of just one can be used for molecular transport. Especially for electroporation of cells packed in a multiple-monolayer pellet, an alternating current pulsing scheme can alleviate the longitudinal shielding effect as explained in the description for FIG. 4. The pulse generator can be controlled by a digital or analog panel. Further, the pulse generator can include a rechargeable battery so that the unit can become cordless when desired.

The monolayer method is beneficial to cells of different sizes. The cells of smaller sizes are more benefited because of their requirement for higher electric field strength in a traditional electroporation. The monolayer method may be conveniently applied to cells that typically grow in suspensions, such as hematopoietic cell lines, lymphocytic cell lines and cells of blood origin.

For adherent cells that usually grow on some supporting substance or structure, they may be temporarily suspended for electroporation. The adherent cells may be removed from their supporting structure by common means such as mechanical dispersing and trypsin treatment. The adherent cells then may be suspended in appropriate medium or buffer and form the monolayer for electroporation.

The adherent cells may also be cultured on the interface between two medium layers 12 and 13 inside the sample container 10. The cultured adherent cells within the sample container 10 may be directly electroporated. However, it is more difficult to control the quality of such electroporations for several reasons. First, the cell surface area variation of adherent cells is much larger than suspension cells and the electrical properties of cells are more variable. Second, it is hard for adherent cells to cover the monolayer 11 uniformly. Cells may be absent in some devoid areas and may be stacked in some crowded area. The cells close to the devoid areas may be subject to increased electrical toxicity. The electroporation efficiency may be decreased in a crowded area because some cells are on top of other cells. Third, the electroporation may only be performed during a specific time when cells reach confluence but not over growing. As a result, the time to perform the electroporation is restricted. Fourth, reproducibility of results can be lower because the time needed for cell culture introduces variation among samples.

Figure 6:
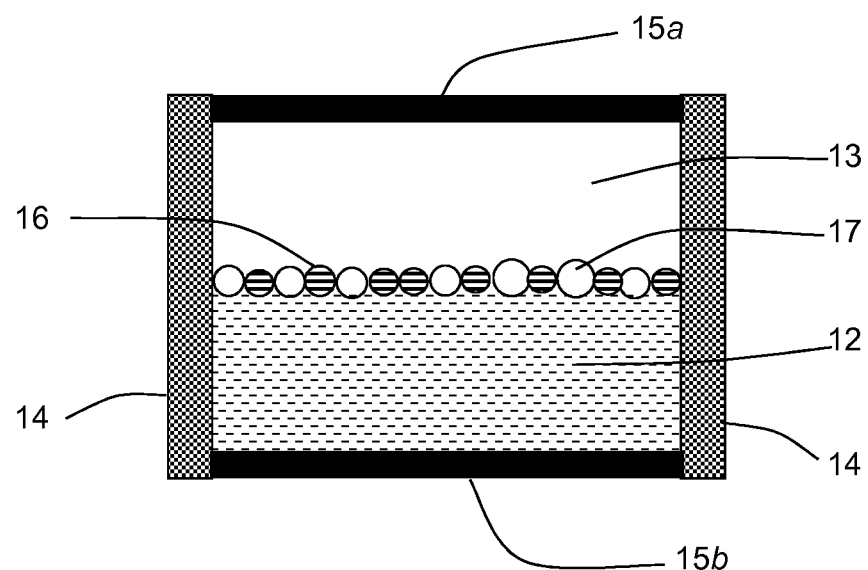
FIG. 6 illustrates the use of cell-mimicking artificial insulator particles in boosting up the total cell number.

If the cell number is low, cell-mimicking artificial insulator particles with a similar diameter may be used to boost up the total cell number. FIG. 6 illustrates the use of artificial insulator particles in electroporation of cells in low numbers. The insulator particles 16 (shaded) are randomly mixed with real cells 17 (open circles). The mixed cell monolayer 11 is formed on the interface of two conductive medium layers 12 and 13. The medium and the cells are contained in an insulator chamber 14 and the electrical pulse is delivered through the electrodes 15a and 15b.

The insulator particles 16 may help form a compact monolayer 11 and restrict the electric current flow as the real cells 17 do. When the number of the insulator particles 16 used exceeds the number of cells in large quantity, the exact number of cells 17 becomes unimportant and the same number of insulator particles 16 may be used with samples containing different number of cells 17, thus simplifying the procedure.

The size of the insulator particles 16 is generally similar to that of the cells 17. It is acceptable that the difference between the diameter of insulator particles 16 and that of the cells 17 is within an order of 10.

The insulator particles 16 may be made of or coated with materials having certain biological properties so that they may be left with the cells 17 after electroporation. The insulator particles 16 may also be made of materials having magnetic properties so that they may be separated by a magnetic method. Other methods of separating the insulator particles 16 from the cells 17 may be based on differential rate of sedimentation or differential density. In certain embodiments, the artificial insulator particles 16 may be other types of real cells, such as, cells that may allow easy separation after electroporation and cells that may be irradiated or drug-treated to lose the cell viability or to stop the cell growth.

The sample container 10 as shown in FIG. 1A is one exemplary container consistent with the disclosed embodiments. Other types of sample containers may also be used.

Figure 7:
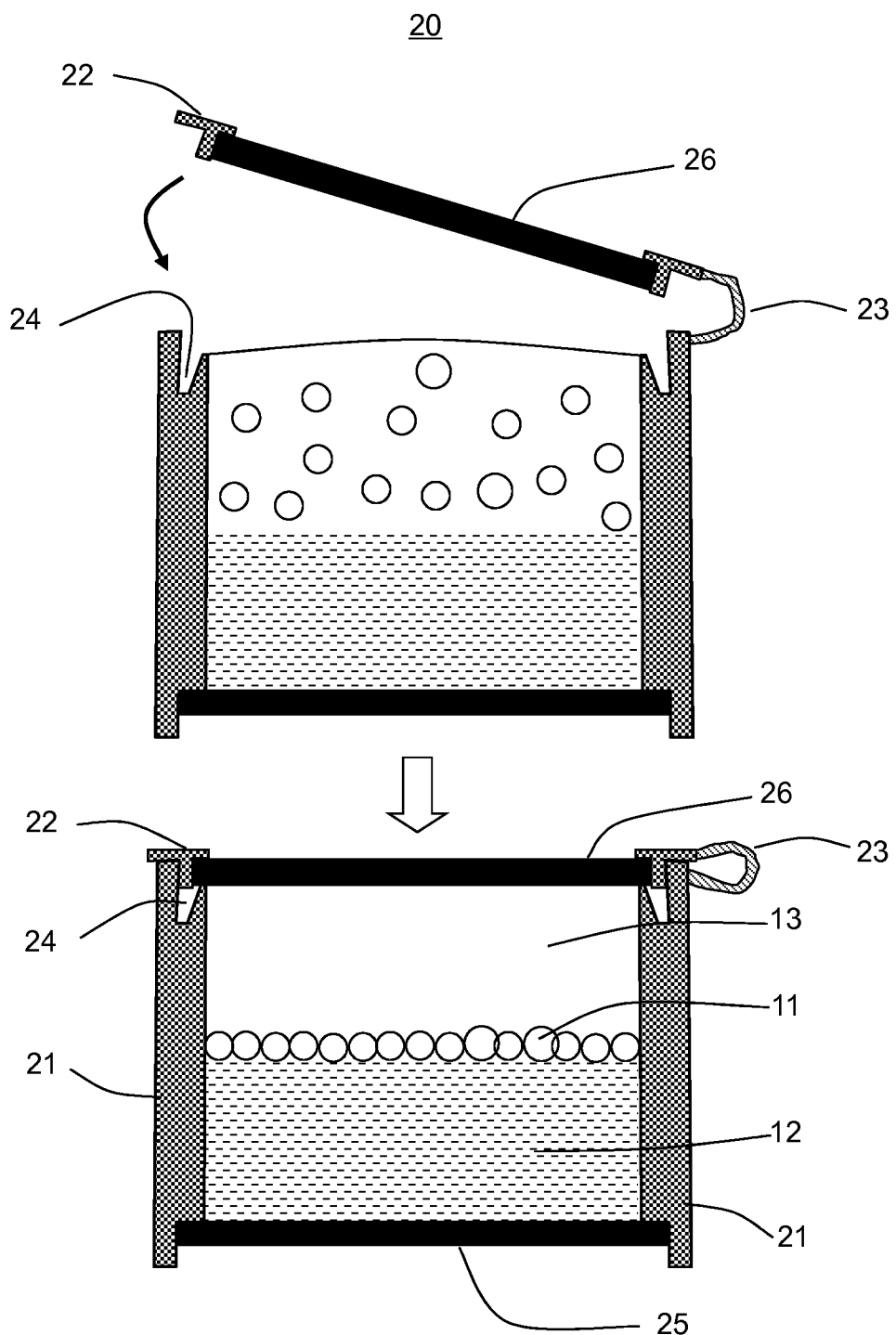
FIG. 7 illustrates an exemplary sample container consistent with the disclosed embodiments.

FIG. 7 illustrates an exemplary sample container 20 consistent with the disclosed embodiments. The sample container 20 includes a fixed electrode 25, a movable electrode 26 that also functions as a sealing cover, a cylindrical insulator chamber 21, an excess-receiving groove 24.

The chamber 21 has an open groove at the bottom end for fixing the electrode 25 and another open groove at the top of the chamber wall to receive the movable electrode 26. The diameter of the electrode 25 may be slightly larger than the diameter of the groove at the bottom end of the insulator chamber 21 so that the electrode 25 may be tightened by the tension generated in the bottom end of the insulator chamber 21. Alternatively the electrode 25 may be fixed to the insulator chamber 21 for sealing of the container bottom by gluing or any other appropriate methods.

The movable electrode 26 is embedded in an open insulator cover 22 that is connected to the main insulator chamber 21 through a flexible linkage 23. The cover 22 may fit in the top groove in the wall of the main insulator chamber 21 tightly, allowing the electrode 26 to cover on an inner rim in the main insulator chamber 21 and seal the sample. To securely seal the medium layers 12 and 13 containing the cell monolayer 11 without air bubbles, the volume of the cell suspension to be added can be slightly larger than the allowed volume in the sealed container 20 so that there is a little excess liquid to ensure a perfect sealing. The excess liquid pushed out by closing down the electrode cover 26 can flow to the excess-receiving groove 24 etched at the top of the wall of the main insulator chamber 21. After electroporation, the cells in the excess liquid may be discarded as they are not electroporated.

While it is good practice to seal the sample inside the container without air bubbles, some small air bubbles can actually be tolerated during electroporation of cells in the monolayer 11 or in multiple monolayers. Since the overall electric field strength in the medium is very low, the disturbance of the electric field by air bubbles near the electrode 26 would only leave a negligible effect on the electric field near the cells on the medium interface. Compared to traditional open cuvettes, a sealed container may be advantageous because the air bubbles produced near electrodes may be compressed and cause less disturbance to the cell sample. A sealed container generally refers to a container that can enclose a sample without an open side and that a liquid sample inside would not flow around when the container is rotated to different orientations.

A cylindrical chamber is relatively easy to manufacture, and round-shaped electrode plates can easily fit in tightly even without the use of any sealing glue. The cylindrical container 20 may be altered or include additional features. While the inside space of the container 20 is cylindrical, the exterior of the container may be in other shapes as long as the inside shape of the container is maintained. The cylindrical container 20 may also be made in different dimensions. In one embodiment, the distance between the electrodes 25 and 26 may be between 1 mm and 50 mm. In another embodiment, the distance between the electrodes 25 and 26 may be between 1 mm and 30 mm. The inner diameter of the main insulator chamber 21 may be between 1 mm and 100 mm.

While cylindrical containers are convenient to manufacture and use, a container 20 for monolayer electroporation may use any suitable shape as long as the cells can form a monolayer on the medium interface or the electrode 25. For example, a rectangular container or container with other shapes would be suitable. A snap-on closing mechanism or other closing mechanism may be used on the rectangular container.

As shown in FIG. 7, the sealing cover includes the electrode 26 encased by the insulator cover 22. Other type of sealing cover may also be used. For example, a sealing cover may be a properly shaped conducting electrode 26 with a snap-on or screw-on closing mechanism.

The insulator cover 22 may be snapped on to close the sample container 20. A locking structure can be used to ensure a tight closure. Other means such as screw-on type closing mechanism may be used. For example, screw threads may be made on the open insulator cover 22 and the main insulator chamber 21 for a tight closure. The cover 22 may tightly fit to the inner rim of the main chamber 21 as shown in FIG. 7, or it may fit on the main chamber 21 by the outer rim. Optionally, a flexible linkage 23 may also be included for convenient closure of the cover 22.

On each of these components of the exemplary sample container 20, there may be markings or handles for convenient handling. The insulator chamber 21 may be made of the materials similar to those making the insulator chamber 14. The electrodes 25 and 26 may be made of the materials similar to those making the electrodes 15*a* and 15*b*.

Figure 8:
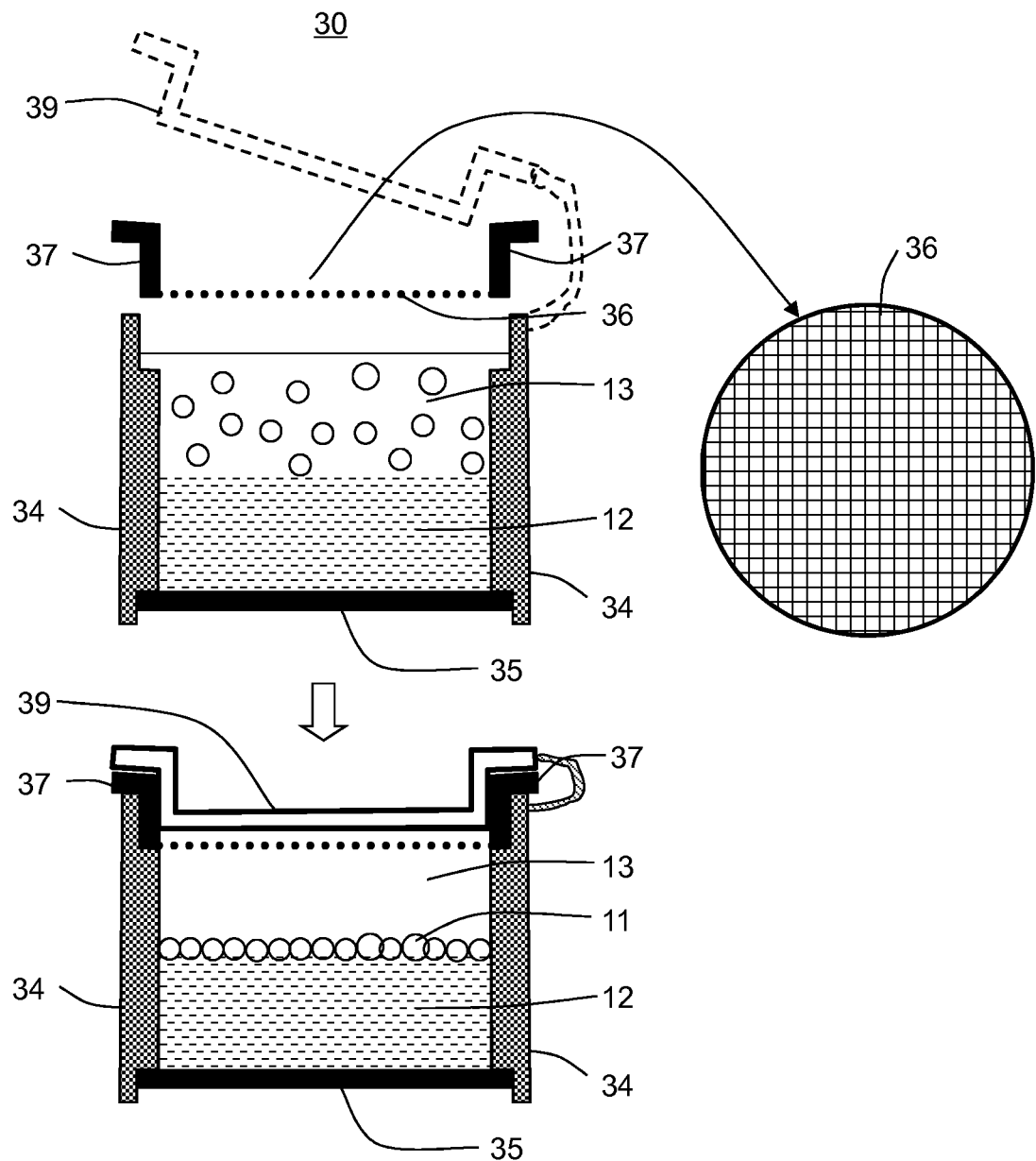
FIG. 8 illustrates an exemplary sample container consistent with the disclosed embodiments.

The present disclosure also contemplates a sample container with open configuration. FIG. 8 illustrates an exemplary sample container 30 consistent with the disclosed embodiments. As shown in FIG. 8, the sample container 30 includes an insulator chamber 34, a bottom electrode 35, a mesh-type electrode 36 with a matching metal connector 37, and a sealing cover 39.

As shown in FIG. 8, cells form a monolayer 11 or multiple monolayers on the interface between the lower medium layer 12 and the upper medium layer 13. The mediums and the cells are contained in the insulator chamber 34 of the container 30. The bottom electrode 35 is fixed in a groove at the bottom end of the insulator chamber 34. The container 30 may take any appropriate shapes such as rectangle. The containers may be arranged in an array for processing of multiple samples.

A mesh-type electrode 36 with a matching metal connector 37 is inserted to a groove at the top of the wall of the insulator chamber 34. The mesh electrode 36 would allow free passage of the cells and it is submerged in the upper medium layer 13 for electroporation of the cells. The mesh electrode 36 may be inserted before or after addition of the cell suspension. In addition, the mesh electrode 36 may be fixed in the container 30 or removably attached to the container 30. The mesh electrode 36 takes the same shape of the container 30 to fit on the container 30. For example, the mesh electrode 36 is rectangular when the container 30 is rectangular.

The open configuration container 30 may be further protected by a sealing cover 39 at the top if necessary. The sealing cover 39 may be made of plastic. Cells may be unloaded either after removing the mesh electrode 36 or in presence of the mesh electrode 36.

The insulator chamber 34 may be made of the materials similar to those making the insulator chamber 11. The electrodes 35, 36 and the connector 37 may be made of the materials similar to those making the electrodes 15*a* and 15*b*.

Figure 9:
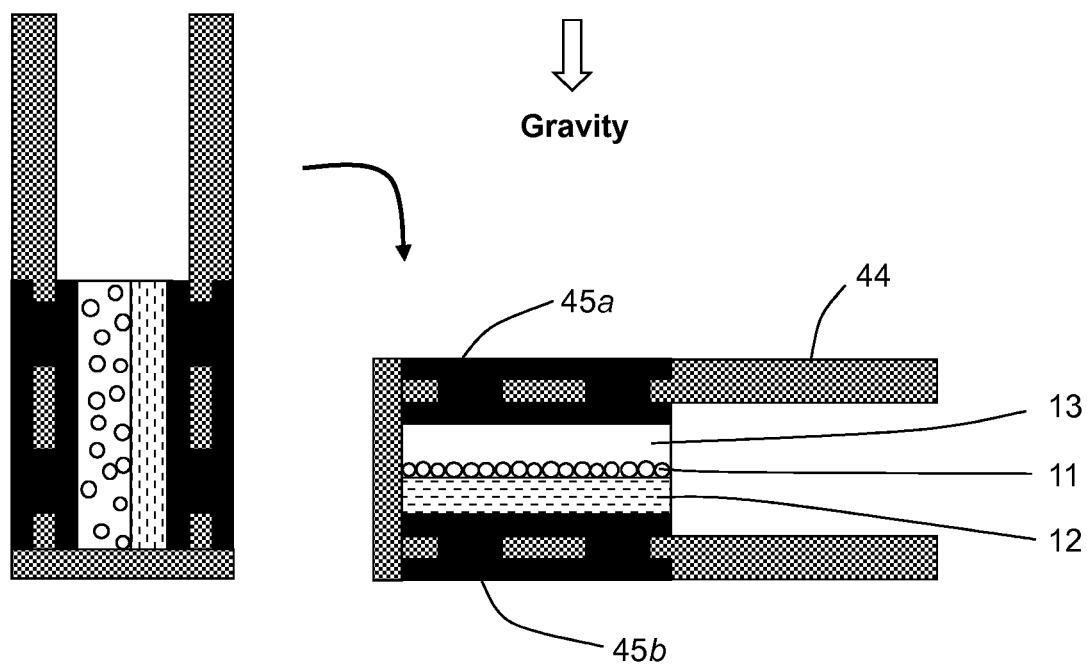
FIG. 9 illustrates an exemplary sample container consistent with the disclosed embodiments.

The present disclosure also contemplates a sample container with fixed electrodes and separate additional cover. FIG. 9 illustrates an exemplary sample container 40 consistent with the disclosed embodiments. As shown in FIG. 9, the container 40 includes an insulator chamber 44, a first fixed electrode 45*a*, a second fixed electrode 45*b*, and pre-formed semi-solid or doused solid lower medium layer 12 within the container 40.

The insulator chamber 44 may be made of the materials similar to those making the insulator chamber 14. The electrodes 45*a* and 45*b* may be made of the materials similar to those making the electrodes 15*a* and 15*b*.

As shown in FIG. 9, a cell suspension fills up the gap between the lower medium layer 12 and the first electrode 45*a* when the container is placed vertically, i.e., the medium interface is vertical. The container 40 is then immediately turned level so that the medium interface becomes horizontal and the cells form the monolayer 11 that settles on the interface between the lower medium layer 12 and the upper medium layer 13. The cell suspension is confined in the open-ended container 40 by natural surface tension of the liquid and the cells may settle down by gravity but not a strong centrifugal force. If a centrifugal force is desired, a sealing cover (not shown in the drawing) may be used to seal the medium layers 12 and 13 on the open side.

To arrange cells into a compact monolayer, preferably a cell suspension containing an appropriate number of cells is placed on top of the lower medium layer 12. Cells may settle on the interface between the lower medium layer 12 and the upper medium layer 13 under the natural gravity or an artificial centrifugal force. Alternatively, a lower medium with higher density can be added to the cell suspension. The lower medium layer 12, the upper medium layer 13, and the cell monolayer 11 may form under the natural gravity or an artificial centrifugal force. It is simple and low-cost to precipitate the cells to the interface by natural gravity. On the other hand, with an artificial centrifugal force stronger than gravity, a cell monolayer or a multiple-monolayer pellet can be formed more quickly and more compactly.

Figure 10:
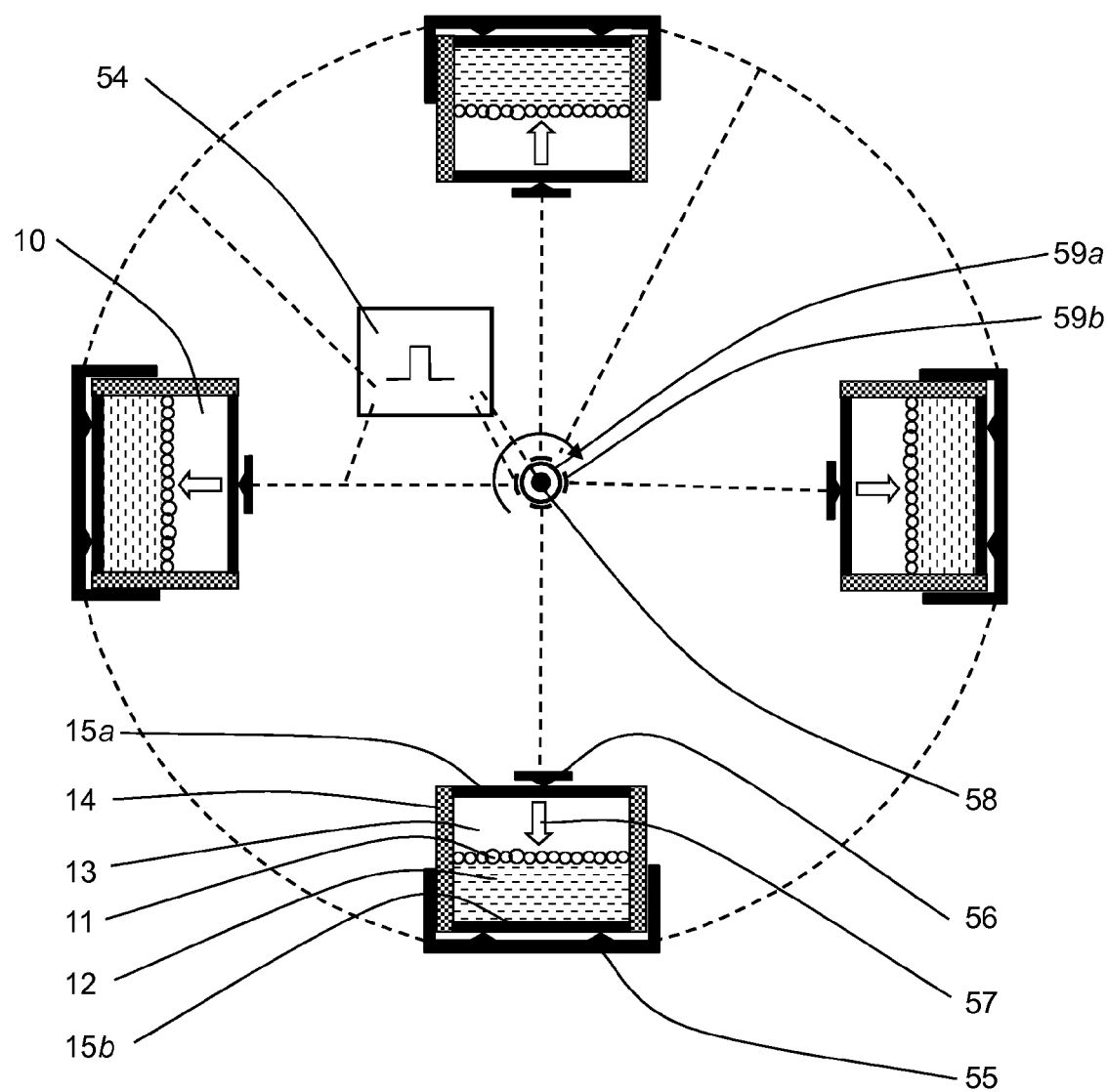
FIG. 10 illustrates an exemplary use of centrifugation in making a compact cell monolayer or multiple monolayers of cells for electroporation or electrical cell fusion consistent with the disclosed embodiments.

FIG. 10 illustrates the use of centrifugation in making a compact cell monolayer or a pellet of cells. The exemplary sample containers 10 with the two electrodes 15*a* and 15*b* and the insulator chamber 14 may be used to hold the two medium layers 12 and 13 and the cell monolayer 11. One or more sample containers 10 can be placed in one rotor with proper balancing. Other exemplary sample containers, such as containers 20, 30, or 40, may be used in centrifugation as well.

An exemplary centrifuge 50 consistent with the disclosed embodiments is shown in FIG. 10. The centrifuge 50 includes a first metal support 55, a second metal piece 56, an axis of rotation 58, an electrical brush 59*a* and 59*b*, and proper in-rotor wiring. Optionally, an in-rotor circuitry 54 may be included to generate an electrical pulse in the rotor.

The first metal support 55 keeps the container in the rotor and makes electrical contact with the bottom electrode 15*b*. The second metal piece 56 is pressed by the centrifugal force to the top electrode 15*a* to make an electrical contact. The two contact points where the metal pieces 55 and 56 contact the sample containers 10 may be wired to the axis of rotation 58 either as a group or individually through the electrical brushes 59*a* and 59*b* on the axis of rotation 58. When an in-rotor circuitry 54 is used, the metal pieces 55 and 56 may be wired to the in-rotor circuitry 54. The two metal pieces 55 and 56 thus function as conductor to deliver an electrical pulse to the sample container 10.

The centrifuge 50 may be a swing-bucket centrifuge or a fixed-rotor centrifuge. During centrifugation, the medium interface or the cell monolayer 10 is substantially perpendicular to the arm of rotation or the direction of centrifugal force as indicated by an open arrow 57. The proper angle can be easily achieved in a self-adjusting swing-bucket rotor or a fixed-angle rotor that positions the medium interface in an electroporation container nearly perpendicular to the arm of rotation. The axis of rotation 58 for a fixed-angle rotor can either be vertical or horizontal. When the axis of rotation 58 is horizontal, the medium interface needs to be substantially perpendicular to the arm of rotation.

Centrifugal force is proportional to the radius of rotation and the square of angular velocity. For a typical rotation radius of several centimeters to several decimeters, a rotation speed of several hundred rpm (revolutions per minute) to several thousand rpm is sufficient for most eukaryotic cells to form a cell monolayer. Other rpm numbers may also be used. For small prokaryotic cells such as bacteria, a rotation speed of several thousand rpm may be needed. The time needed for centrifugation can be from seconds to minutes. Other time may also be used. The acceleration of rotation can be made gentle, so that cells do not move sideways on the medium interface in a container. For a fixed-angle rotor that positions the medium interface vertically, rotation should start promptly so that cells in suspension do not sink to one side to cause unevenness in cell distribution.

Theoretically, a flat medium interface in a rotor produces slightly uneven centrifugal force because of the differential rotation radius. This would not be a significant factor if the time of centrifugation is not prolonged. A substantially even cell distribution may be achieved through a longer rotation arm length, a medium interface that reduces sideway cell movements and some settling-down time before centrifugation. A sample container with curved electrodes may be made. A curved medium interface may be formed within the container that has equal radius of rotation on all points. A container with a full-circle cylindrical medium interface rotating around its own axis would ideally provide equal radius of rotation on all interface points and it can use any acceleration setting without problem of sideway cell movements.

As shown in FIG. 10, the metal pieces 55 and 56 may be wired to the axis of the rotation 58 to provide an electrical pulse to electroporate the cells on the cell monolayer 11 during centrifuge.

An electrical pulse can be delivered after the cells are brought into the monolayer 11 or a multiple-monolayer pellet. When the centrifuge 50 is used, an electrical pulse can be delivered after centrifugation or during centrifugation. To pulse after centrifuge, a common laboratory centrifuges without in-rotor electrical wirings may be used with suitable adapters for holding the electroporation containers in the rotor. However, the sample containers 10 need to be very carefully taken out of the centrifuge 50 to avoid disturbing the cell monolayer 10 or pellet before pulsing. On the other hand, delivery of an electrical pulse during centrifugation is advantageous in that the pulsing condition would be more reliable.

After the delivery of an electrical pulse, cells can be removed from the sample container 10 or remain in the container 10 if the medium for electroporation is also suitable for cell maintenance. A centrifuge and a pulse generator can be integrated into one machine, providing easy portability and convenient control.

The carbon brush or electrical brush 59a and 59b can be used to wire the final electrical pulse from the pulse generator directly to samples in a centrifuge rotor. Alternatively, the final electrical pulse for the samples can be generated by the in-rotor circuitry 54 to avoid any signal noise from the electrical brushes 59a and 59b. The in-rotor circuitry 54 can be constructed near the rotation axis 58 so that it is not subject to a high centrifugal force. When the in-rotor circuitry 54 is used, the electrical brushes 59a and 59b can be used to receive electrical energy and control instructions and they are not in the final pulse delivery loop. Contactless electrical power delivery can also be achieved using magnetic energy transfer to avoid signal noise from the electrical brushes 59a and 59b. When the in-rotor circuitry 54 is used, wireless radio signals can be used to control the pulsing in the rotor.

Figure 11:
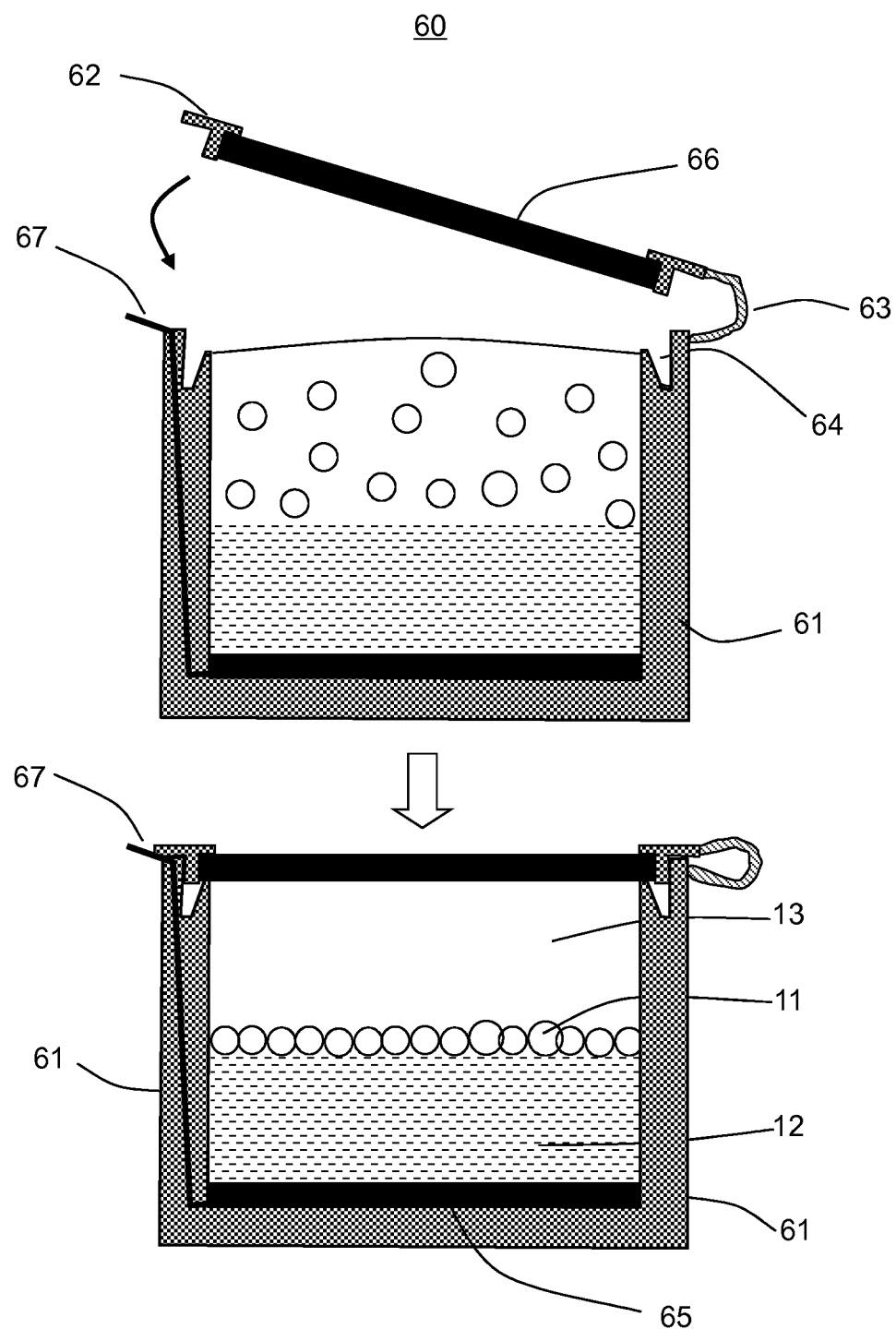
FIG. 11 illustrates an exemplary sample container consistent with the disclosed embodiments.

FIG. 11 illustrates an exemplary container 60 consistent with the present disclosure. As shown in FIG. 11, the bottom electrode 65 is enclosed in the insulator chamber 61. An insulated metal wire 67 connects to the bottom electrode 65. The upper electrode 66 encased by an open cover 62 can close onto the main insulator chamber 61 and seal two medium layers 12 and 13 and the cell monolayer 11. The cover 62 maybe be linked the main chamber by a linker 63. A groove 74 may be made in the main insulator chamber to hold any excess sample. An electrical pulse is delivered through the electrodes 66 and 67. This configuration may be useful in preventing sample leakage during centrifugation.

In addition, the present disclosure may be used for electrical cell fusion. When electrical cell fusion is the objective of the electroporation, a double-monolayer configuration with roughly two cell monolayers may be used in a sample containers similar to the sample container used for electroporation, such as the exemplary sample container 10, 20, 30, 40 or 60. Preferably, each layer contains one type of cell, but mixing the two types of cells are acceptable although the efficiency of fusion may be lower.

The double-monolayer may be formed sequentially or together by taking advantage of differential sedimentation speeds, i.e., one type of cell can settle down first and the other one can follow afterwards. A container with a mesh-type electrode may be convenient for making two monolayers of different cells. The first cell suspension may be added to a container just up to the mesh electrode and the cells are collected onto the lower medium interface. Then the second cell suspension may be added above the mesh electrode so that they may be arranged evenly on top of the first cell monolayer. Another possible way of making two sequential monolayers is to use two cell suspensions in two different mediums that can form an interface and the second cell suspension can be added after the first cell suspension is already in a monolayer.

The double-monolayer in suitable buffers can then be treated by a suitable electrical pulse to promote cell fusion. The delivery of electrical pulse may occur during centrifugation. Because there is no target substance to be delivered to the cells during electrical cell fusion, saving reagents is not an objective. Therefore a sample container for cell fusion may have a larger distance between the two electrodes so that it is easier to make two monolayers of different cells sequentially. Furthermore, two types of cell monolayers can form a sandwich of alternating cell layers with three or more cell layers for electrical cell fusion by repeating the steps of removing centrifuged medium and adding more cell suspension.

Figure 12:
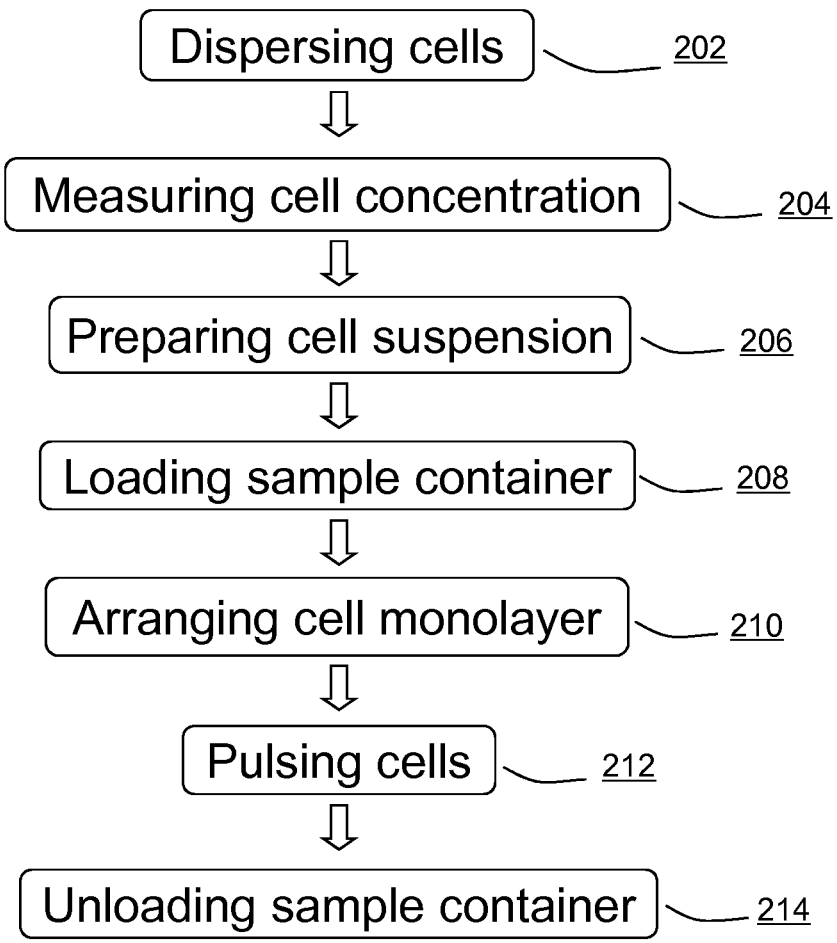
FIG. 12 illustrates an exemplary process of electroporation consistent with the disclosed embodiments.

FIG. 12 illustrates an exemplary process 200 for the monolayer electroporation consistent with the disclosed embodiments. In the beginning, cells are dispersed in a suspension (202). For adherent cells, they can be lifted and dispersed into a suspension. Cells can be washed when desired. Further, the cell concentration can be determined by a counting method (204). An appropriate number of cells are then taken for a monolayer or for multiple monolayers. Further, the cell suspension is adjusted to a suitable volume for a sample container (206). Target substances to be delivered may be included in the cell suspension before loading the cell suspension to sample containers. Further, the cell suspension is loaded in a sample container (208).

After loading the cell suspension in a sample container, a cell monolayer is arranged (210). If the cell monolayer is to be made by gravity mediated natural sedimentation, the sample containers need to be placed on a level surface for a certain period of time. The time needed to form a monolayer may be determined empirically using the methods discussed in paragraph [0068]. For example, the formation of the monolayer may be observed under microscope. If the cell monolayer is to be made by centrifugation, the sample containers can be placed in a centrifuge. After the formation of the cell monolayer, the cells are treated by an electrical pulse (212). The electrical pulse treatment may be performed after centrifuge or during centrifuge if a centrifuge is used to form the cell monolayer. After the electrical pulse treatment of the cells, the cells are unloaded from the sample containers (214). If the electrical pulse treatment is during the centrifuge, the centrifuge is stopped before the unloading of the cells. For electrical cell fusion, there may be an additional step in making the cell double-monolayer and the buffers and the electrical pulse can be different from those typically used for the purpose of substance delivery.

Figure 13A:
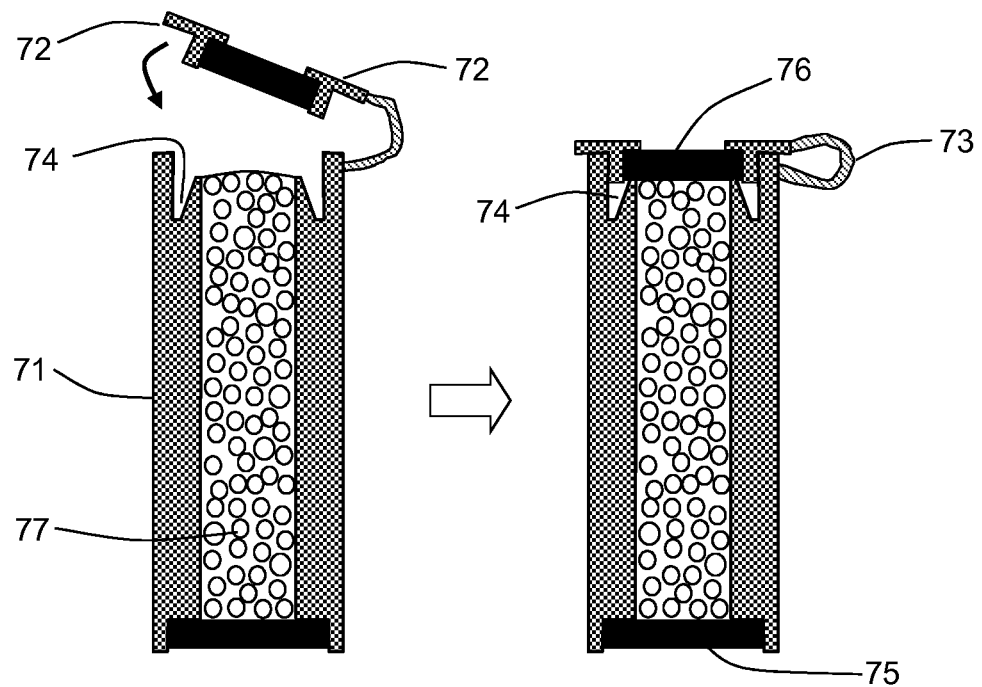
FIG. 13A illustrates an exemplary sample container consistent with the disclosed embodiments.

The present disclosure may also be applicable to electroporation in cell suspension. FIG. 13A illustrates an exemplary sample container 70 consistent with the disclosed embodiments, which may be used for electroporation of a cell suspension. As shown in FIG. 13A, the container 70 includes a cylindrical insulator chamber 71, a fixed electrode 75, a movable electrode 76 that also functions as a sealing cover, an open insulator cover 72, and an excess-receiving groove 74.

The insulator chamber 71 has an open groove at the bottom end for fixing the electrode 75 and another open groove 74 at the top of the wall of the chamber 71 to receive the movable electrode 76. The diameter of the electrode 75 may be slightly larger than the diameter of the groove at the bottom end of the insulator chamber 71 so that the electrode 75 can be tightened by some tension generated in the bottom end of the insulator chamber 71. Alternatively the electrode 75 may be fixed to the insulator chamber 71 for sealing of the container bottom by gluing or any other appropriate methods.

The movable electrode 76 is embedded in the open insulator cover 72 that is connected to the main insulator chamber 71 through a flexible linkage 73. The cover 72 is capable of fitting in the top groove 74 in the wall of the main insulator chamber 71 tightly, allowing the electrode 76 to cover on an inner rim in the main insulator chamber 71 and seal the sample. To securely seal the cell suspension 77 without air bubbles, the volume of the cell suspension to be added may be slightly larger than the allowed volume in the sealed container so that there is a little excess liquid to ensure a perfect sealing. The excess liquid pushed out by closing down the electrode cover 76 can flow to the excess-receiving groove 74 etched at the top of the wall of the main insulator chamber 71. After electroporation, the cells in the excess liquid can be discarded as they are not electroporated. While it is a good practice to seal a cell suspension inside the container 70 without air bubbles, some small air bubbles may actually be tolerated as long as the small air bubbles only occupy a small portion of the electrode surface.

The understandings of the longitudinal shielding effect and the lateral enhancing effect can also help to improve the electroporation efficiency for cells in suspensions. For cell types of larger sizes, they require lower field strength to obtain effective electroporations and cell heterogeneity caused by proximal cell-to-cell electrical interactions may not be beneficial for electroporation efficiency. However, for more common cell types of smaller sizes that require a high field strength to obtain effective electroporation, cell heterogeneity caused by proximal cell-to-cell electrical interactions can instead be very beneficial for cell electroporation.

For smaller cells, increasing the cell concentration in the suspension may increase the effect of lateral enhancing. Simultaneously longitudinal shielding effect may be increased as well. The increased longitudinal shielding may be a worthy tradeoff to the increased lateral enhancing effect. The longitudinal shielding effect may be alleviated by an alternating-current pulsing scheme.

The preferred percentage of total cell volume in the cell suspension would be around or larger than 10%. When there are not enough cells, artificial insulator particles may be used similar to those described for the monolayer based methods.

For improved electroporation of cell suspensions, the exemplary sample container 70, or other sample containers which are similar to those described for monolayer based methods may be used. The container 70 dedicated for electroporation of cell suspensions tends to have longer distance between the electrodes 75 and 76 so that fewer cells are within the immediate vicinity of the electrodes to reduce electrochemical toxicities to the cells. The distance between the electrodes 75 and 76 is preferred to be between 3 mm to 100 mm, and a distance between 5 mm to 50 mm is further preferred.

The container 70 may be in a shape of a cylinder. The diameter of the cross section of the container 70 may be larger than 1 mm. In certain embodiments, the diameter of the cross section of the container 70 may be ranged from 1 to 20 mm. Other diameter value may also be used. The container 70 may also be in other shape with a comparable cross section area to that of a cylindrical container.

The movable electrode such as the electrode 76 in the container 70 may be used on both ends of an insulator chamber, especially when the inner diameter of the container is small or the distance between the electrodes is quite long. For such a container 70, it may not be convenient to load a sample with just one movable electrode. Since the cells near the electrodes are subject to significant electrochemical toxicity, some markings may be made on the insulator chamber 71 as indicators of the harmed cells to be discarded. The container 70 may also be connected to a sample injection system to enable continuous processing of a cell suspension sample that flows into the container.

When the container 70 has a relatively long distance between the electrodes 75 and 76, a high voltage would be needed to maintain a comparable electric field strength. The seeming disadvantage to require the pulse generator to deliver a higher voltage may be less of a problem.

For example, to electroporate a suspension of a human cell line, 200 volts is needed for a 0.2 ml sample in a 4 mm-gap cuvette with exponential discharge from a capacitor of about 1000 μf. If the same 0.2 ml cell suspension is placed in a longer container with 2 cm electrode distance (5 times of cuvette gap distance), the voltage required would be 1000 volts, but a capacitor of only 40 μF (¹⁄₂₅ of 1000 μF) is needed because the electric energy from a capacitor follows the equation of $$E=0.5U^2C$$

where E is electric energy, U is voltage and C is capacitance. Therefore a high voltage pulse generator is actually easy to manufacture because it needs a much smaller capacitor to store a similar amount of energy. Similarly, it would not be difficult to generate other wave forms of higher voltages.

Very small cells such as bacteria need a very high electric field strength such as 20,000 V/cm to be electroporated in a low-conductance liquid such as water. Traditionally bacteria electroporation is done in a cuvette with a short electrode distance of 1 mm or 2 mm so that a voltage of less than 3,000 V is usually needed. To electroporate very small cells such as bacteria in the container 70, an ultra-high voltage may be needed. Ultra-high voltage, as used in this disclosure, refers to the voltage that is higher than 5,000 V and often in the range of 10,000 to 30,000 V typically used for electroporation of very small cells. A pulse generator capable of delivering tens of thousands volts may not be difficult to manufacture, since a very low capacitance would be needed to store the energy under ultra-high voltages. The pulse generators can be equipped with rechargeable batteries to become cordless and facilitate easy mobility.

The sealable container 70 with longer electrode distance may effectively prevent electric arcs. In a traditional cuvette, unevenly distributed ionic solutes may form small leaky areas for electric current that short-circuit the two electrodes nearby. In a sealed container with a longer electrode distance, even when a small leaky area forms, it would be far less likely to extend from one electrode to the other to cause short-circuit. Even when there are small air bubbles trapped near the electrodes, they would not cause an arc because they do not extend from one electrode to the other. Therefore, the longer sealed container 70 would be advantageous in suppressing the formation of an electric arc.

Another advantage of the longer container 70 is that it is easier to manufacture the container 70 in high precisions. A 50 µm distance error is 5% for a 1 mm cuvette, but it is only 0.25% for a 2 cm long container.

Figure 13B:
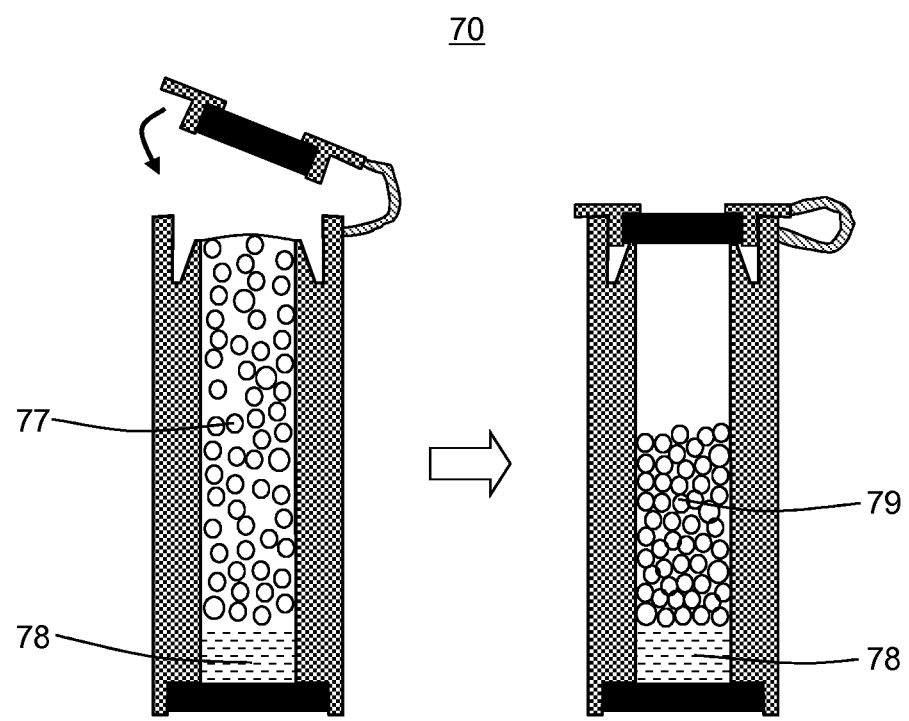
FIG. 13B illustrates an exemplary use of an exemplary lower medium layer for electroporation consistent with the disclosed embodiments.

FIG. 13B illustrates an exemplary use of a lower medium layer 78 in the container 70 for electroporation of cell suspension consistent with the disclosed embodiments. As shown in FIG. 13B, the lower medium layer 78 is formed. A cell suspension 77 is loaded on the lower medium layer 78. The cell suspension 77 may be brought into a pellet 79.

The lower medium layer 78 is similar to the one used for monolayer method of electroporation, such as the lower medium layer 12 in FIG. 1A. The lower medium layer 78 physically keeps cells away from the electrode 75. Another medium layer similar to 78 can be used on the upper electrode as well, especially when the container is intended for electroporation of a cell suspension, so that both ends of the cell suspension are protected from direct exposure to the electrodes. The cell suspension 77 may be electroporated directly in this container, or the cells in the suspension may be brought into the pellet 79 to increase the cell concentration. While the container 70 for electroporation of a cell suspension tends to have longer distance between the electrodes 75 and 76, the container 70 dedicated for electroporation of the cell pellet 79 can have a shorter distance between the electrodes 75 and 76. The pellet 79 can be made by the natural gravity or by centrifugation. If a centrifuge is used, pulsing of the cell pellet 79 can take place after centrifugation or during centrifugation, similar to the methods described for monolayer and multiple-monolayer electroporations in the centrifuge 50. The pellet 79 can be electroporated with high efficiency and low toxicities to the cells at a lower voltage than what is need for electroporation of the same cells in a suspension. The pulse generators can be equipped with rechargeable batteries to facilitate easy mobility and the variations of the pulse generators described for monolayer based electroporation may also be applied for electroporation of cells in suspensions or pellets. Artificial insulator particles may also be used with the real cells for making cell pellets.

The present disclosure provides electroporation devices and methods that can achieve high-efficiency and low toxicities in electroporation. The devices and methods according to the present disclosure offer advantages over other methods and devices. For example, the devices and methods according to the present disclosure have certain advantages over the capillary electroporation.

Figure 14:
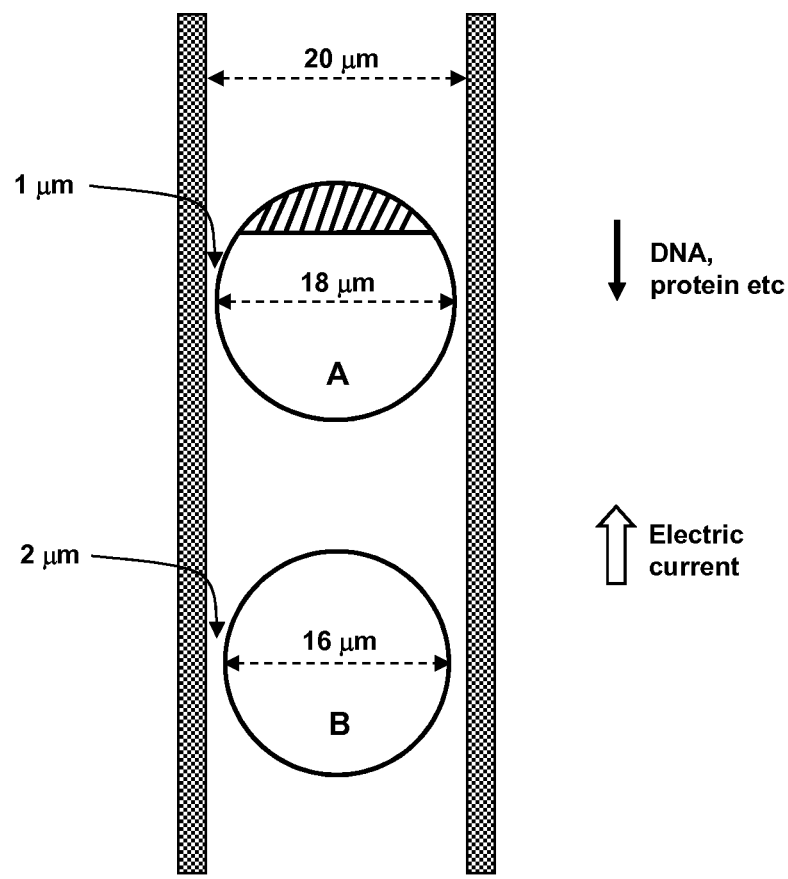
FIG. 14 illustrates an exemplary capillary assisted electroporation.

FIG. 14 illustrates an exemplary capillary assisted electroporation. As shown in FIG. 14, the electroporation is carried out in a capillary with an inner diameter of 20 µm. Two cells, cell A and cell B, are located within the capillary. Cell A has a diameter of 18 µm, and cell B has a diameter of 16 µm.

As shown in FIG. 14, the smallest distance between the cell A and the capillary wall is 1 µm and the smallest distance between the cell B and the capillary wall is 2 µm. The capillary wall is an insulator so that the electric current is restricted to the gap between the cell and the capillary wall. The same total electric current flows through the gaps around the cell A and the cell B.

Because the cross-sectional area of the gap around cell B is about twice of the cross-sectional area of the gap around cell A, the electric field strength in the gap around cell B is only about half of the field strength in the gap around A. Therefore, the transmembrane potential of the cell A beyond the gap area is about twice (200%) of the transmembrane potential of the cell B, although the diameter of A is only ⅛ (12.5%) more than the diameter of B. In the capillary, cell A is benefited with the lateral enhancing effect from the capillary wall. However, it is very difficult for B to be electroporated, although B is only slightly smaller. Even with an alternating current pulsing scheme, the cell B would have about half of the transmembrane potential of A. As a result, cell B still would not be effectively electroporated. If the diameter of A becomes 19 µm and its gap becomes 0.5 µm, the transmembrane potential of A would become about 400% of B, suggesting that a capillary could introduce a significant amount of cell heterogeneity in electroporation efficiency.

A capillary thus works by employing the lateral enhancing effect from the capillary wall. It works better when the inner diameter is smaller because a higher portion of the cells are located within the immediate vicinity of the capillary wall for a smaller capillary. The compact monolayer based electroporation method reduces cell heterogeneity in electroporation. By comparison, the capillary method of electroporation exaggerates the cell heterogeneity in electroporation and it is inherently limited. Primarily utilizing the lateral enhancing effect from the concentrated cells themselves in a suspension or a pellet as described in the present disclosure can be advantageous in both electroporation efficiency and cost effectiveness.

While various embodiments and the accompanying figures have been shown and described, it is understood that they are not intended to limit the scope of the present invention.

I claim:

1. An apparatus for electroporation of biological cells, comprising a sample container for holding a sample of biological cells for electroporation, the sample container comprising:
    an insulator chamber that forms the body of the container to hold the cells, the insulator chamber having a plurality of sides;
    a first electrode being in a cover configured to removably cover the chamber;
    a top groove on a top of one side of the insulator chamber, and
    a second electrode, wherein:
    the first electrode and the second electrode receive an electrical pulse from an electrical pulse generator to electroporate the cells;
    wherein the cover is shaped to fit with the groove to seal the chamber through a dosing mechanism selected from the group consisting of a snap-on mechanism and a screw-on mechanism;
    wherein the first electrode in the cover covers an inner rim of the groove on the side of the chamber.

2. The apparatus of claim 1, further including:
    a first conductive medium layer containing an aqueous solution having solute ions to conduct an electric pulse to the sample of biological cells,
    a surface formed on the first conductive medium layer, wherein:
    the surface is separated from the first electrode and the second electrode, and the first conductive medium layer conducts an electric pulse through the solute ions to the cells through substantially the entire surface.

3. The apparatus of claim 2, further comprising:
a precast porous matrix, wherein:
the first conductive medium layer is cast in the porous matrix.

4. The apparatus of claim 1, wherein:
the top groove has an excess-receiving groove on a first end of the wall of the insulator chamber for receiving extra liquid.

5. The apparatus of 1, further comprising:
an ultra-high voltage pulse generator for electroporation of the biological cells in the insulator chamber through the electrodes.

6. The apparatus of claim 5, wherein:
the pulse generator is capable of generating a pulse of ultra-high voltage of over 5,000volts.

7. The apparatus of claim 5, wherein:
the pulse generator is capable of generating a pulse of ultra-high voltage of over 8,000volts.

8. The apparatus of claim 5, wherein:
the pulse generator is capable of generating a pulse of ultra-high voltage of over 10,000 volts.

9. The apparatus of claim 1, further comprising:
a flexible linkage for linking the removable cover to the insulator chamber.

* * * * *